US009868731B2

(12) United States Patent
Park et al.

(10) Patent No.: US 9,868,731 B2
(45) Date of Patent: Jan. 16, 2018

(54) INDOLE AMIDE COMPOUND AS INHIBITOR OF NECROSIS

(71) Applicant: LG CHEM, LTD., Seoul (KR)

(72) Inventors: Heui Sul Park, Daejeon (KR); Sun Young Koo, Daejeon (KR); Hyoung Jin Kim, Daejeon (KR); Sung Bae Lee, Daejeon (KR); Hyo Shin Kwak, Daejeon (KR); Seung Yup Paek, Daejeon (KR); Soon Ha Kim, Daejeon (KR)

(73) Assignee: LG CHEM, LTD., Seoul (KR)

(*) Notice: Subject to any disclaimer, the term of this patent is extended or adjusted under 35 U.S.C. 154(b) by 0 days.

(21) Appl. No.: 14/913,140

(22) PCT Filed: Aug. 21, 2014

(86) PCT No.: PCT/KR2014/007761
§ 371 (c)(1),
(2) Date: Feb. 19, 2016

(87) PCT Pub. No.: WO2015/026172
PCT Pub. Date: Feb. 26, 2015

(65) Prior Publication Data
US 2016/0194313 A1 Jul. 7, 2016

(30) Foreign Application Priority Data

Aug. 22, 2013 (KR) .................. 10-2013-0099967

(51) Int. Cl.
*C07D 417/12* (2006.01)
*C07D 403/12* (2006.01)
*C07D 405/14* (2006.01)
*C07D 403/06* (2006.01)
*C07D 209/42* (2006.01)
*A61K 31/4045* (2006.01)
*A61K 31/427* (2006.01)
*A61K 31/4439* (2006.01)
*A61K 31/454* (2006.01)
*A61K 31/5377* (2006.01)
*A61K 31/541* (2006.01)
*A61K 45/06* (2006.01)
*C07D 401/12* (2006.01)
*C07D 401/14* (2006.01)
*C07D 403/14* (2006.01)

(52) U.S. Cl.
CPC ........ *C07D 417/12* (2013.01); *A61K 31/4045* (2013.01); *A61K 31/427* (2013.01); *A61K 31/4439* (2013.01); *A61K 31/454* (2013.01); *A61K 31/5377* (2013.01); *A61K 31/541* (2013.01); *A61K 45/06* (2013.01); *C07D 209/42* (2013.01); *C07D 401/12* (2013.01); *C07D 401/14* (2013.01); *C07D 403/06* (2013.01); *C07D 403/12* (2013.01); *C07D 403/14* (2013.01); *C07D 405/14* (2013.01)

(58) Field of Classification Search
CPC ... C07D 417/12; C07D 403/12; A61K 31/427
See application file for complete search history.

(56) References Cited

U.S. PATENT DOCUMENTS

| 5,767,283 A | 6/1998 | Yoshino et al. |
| 2008/0096877 A1 | 4/2008 | Yasuma et al. |
| 2009/0247746 A1 | 10/2009 | Yasuma et al. |

FOREIGN PATENT DOCUMENTS

| EP | 2 230 238 A2 | 9/2010 |
| JP | 2012-107001 A | 6/2012 |
| WO | WO 95/07276 A1 | 3/1995 |
| WO | WO 02/072548 A2 | 9/2002 |
| WO | WO 2004/018428 A1 | 3/2004 |
| WO | WO 2004/018461 A2 | 3/2004 |
| WO | WO 2006/112549 A1 | 10/2006 |

OTHER PUBLICATIONS

Bessard, Y., "Process Development of 5-Methoxy-1H-indole-2-carboxylic Acid from Ethyl 2-Methylmalonate," Organic Process Research & Development, 1998, vol. 2, No. 4, pp. 214-220.
Clemens, J.J. et al, "Synthesis of benzimidazole based analogues of sphingosine-1-phosphate: discovery of potent, subtype-selective S1P4 receptor agonists," Bioorganic & Medicinal Chemistry Letters, 2004, vol. 14, pp. 4903-4906.
Ino, A. et al, "Synthetic studies of thiazoline and thiazolidine-containing natural products—1. Phosphorus pentachloride-mediated thiazoline construction reaction," Tetrahedron, 1999, vol. 55, pp. 10271-10282.
Klotz, E.J.F. et al, "Homo- and Hetero-[3]Rotaxanes with Two π-Systems Clasped in a Single Macrocycle," J. Am. Chem. Soc., 2006, vol. 128, pp. 15374-15375.
Kreamer, B.L. et al, "Use of a Low-Speed Iso-Density Percoll Centrifugation Method to Increase the Viability of Isolated Rat Hepatocyte Preparations," In Vitro Cellular & Development Biology, Apr. 1986, vol. 22, No. 4, pp. 201-211.
Proskuryakov, S.Y. et al, "Necrosis Is an Active and Controlled Form of Programmed Cell Death," Biochemistry (Moscow), 2002, vol. 67, No. 4, pp. 387-408.
Seglen, P.O., "Preparation of Rat Liver Cells," Experimental Cell Research, 1972, vol. 74, pp. 450-454.
Starcevic, K. et al, "Synthesis, Crystal Structure Determination and Antiproliferative Evaluation of Novel Benzazoyl Benzamides," Heterocycles, 2006, vol. 58, No. 11, pp. 2285-2299.

(Continued)

*Primary Examiner* — Craig Ricci
*Assistant Examiner* — Christopher R Stone
(74) *Attorney, Agent, or Firm* — Birch, Stewart, Kolasch & Birch, LLP

(57) ABSTRACT

The present invention relates to an indole amide compound represented by formula (1), a pharmaceutically acceptable salt or isomer thereof, a composition for prevention or treatment of necrosis and necrosis-associated diseases, and a method for preparing the composition, the composition comprising the indole compound or the pharmaceutically acceptable salt or isomer thereof as an active ingredient.

18 Claims, No Drawings

(56) References Cited

OTHER PUBLICATIONS

You, S.L. et al, "Total Synthesis of Dendroamide A: Oxazole and Thiazole Construction Using an Oxodiphosphonium Salt," J. Org. Chem., 2003, vol. 68, pp. 9506-9509.

International Search Report, issued in PCT/KR2014/007761, dated Jan. 19, 2015.

Bates, G.W., et al, "2,7-Functionalized Indoles as Receptors for Anions," Journal of Organic Chemistry, 2007, vol. 72, pp. 8921-8927.

CAS Registry No. 1285596-41-9, Database Registry [Online], Apr. 25, 2011, Retrieved from: STN.

CAS Registry No. 1341667-99-9, Database Registry [Online], Nov. 6, 2011, Retrieved from: STN.

CAS Registry No. 1410899-62-5, Database Registry [Online], Dec. 4, 2012, Retrieved from: STN.

Engelhardt, H., et al, "Detailed structure activity relationship of indolecarboxamides as H4 receptor ligands," European Journal of Medicinal Chemistry, 2012, vol. 54, pp. 660-668.

Extended European Search Report for Appl. No. 14838146.0 dated Dec. 19, 2016.

Makuc, D., et al, "Conformational changes of functionalised indole receptors upon their interaction with anions," Supramolecular Chemistry, 2010, vol. 22, pp. 603-611.

Makuc, D., et al, "The Halide Binding Behavior of 2-Carbamoyl-7-ureido-1H-indoles: Conformational Aspects," European Journal of Organic Chemistry, 2009, No. 28, pp. 4854-4866.

Rether, C., et al, "Carboxylate Binding by Indole-Based Guanidinium Receptors: Acylguanidinium Cations are Better than Aromatic Guanidinium Cations," European Journal of Organic Chemistry, 2011, No. 8, pp. 1459-1466.

Revesz, L., et al, "Novel CCR1 antagonists with oral activity in the mouse collagen induced arthritis," Bioorganic & Medicinal Chemistry Letters, 2005, vol. 15, pp. 5160-5164.

Scheuerman, R.A., et al, "The reduction of aromatic nitro groups on solid supports using sodium hydrosulfite ($Na_2S_2O_4$)," Tetrahydron Letters, 2000, vol. 41, pp. 6531-6535.

INDOLE AMIDE COMPOUND AS INHIBITOR OF NECROSIS

TECHNICAL FIELD

The present invention relates to an indole amide compound of Formula (1), a pharmaceutically acceptable salt or isomer thereof, and a composition and a method of preparing a composition for the prevention or treatment of cellular necrosis and necrosis-associated diseases comprising the same as an active ingredient.

BACKGROUND ART

Most researches associated with cell death have been focused on apoptosis of cells, also known as programmed cell death (PCD). With the discovery of the enzyme caspase, a number of pharmaceutical companies have promoted the development of drugs utilizing caspase inhibitors during the past 10 years. However, the current status is that no drugs have been approved by the FDA. This is because the apoptosis of cells is a cell death which occurs under physiological circumstances, and such a cell death may be due to the defense mechanism for maintaining homeostasis in the body. In contrast, necrosis is a cell death which mainly occurs under pathologic circumstances, and in most cases it is characterized by an accompanying inflammatory response. Necrosis has been known as an uncontrolled cell death for a long time, but according to recent research (Proskurykakov S Y et al., 2002, Biochemistry) typical diseases caused by necrosis include ischemic (e.g., myocardial infarction, stroke, renal infarction), neurodegenerative and inflammatory diseases. Since it is believed that necrosis is an uncontrolled, accidental cell death under pathologic circumstances, researches on the functional mechanism, molecular targets, signal transduction systems, etc. thereof have rarely been conducted. Therefore, there arises a compelling need to discover and develop necrosis-inhibiting substances for the treatment of ischemic, neurodegenerative, and inflammatory diseases which are caused by necrosis, and to elucidate biological, pathological causes of necrosis.

The indole derivatives according to the present invention have very useful structures from a medical viewpoint, and many publications have reported the research results with reference to these structures. Among the research results, the following are the most representative: International Publication No. WO 2006/112549 reported some indole derivatives having activity for glucokinase, International Publication No. WO 95/07276 reported indole derivatives useful as anti-tumor agents and as inhibitors against the production of cardiovascular system, and International Publication No. WO 2004/018428 reported indole derivatives useful as antibiotics.

DISCLOSURE OF INVENTION

Technical Problem

Accordingly, the present inventors have extensively studied under the above-mentioned technical background to develop new compounds that exhibit an effect of prevention or treatment and amelioration of cellular necrosis and necrosis-associated diseases, and are particularly useful for the prevention or treatment of hepatic diseases. As a result thereof, they confirmed that the indole amide derivatives of Formula (1) as explained below show a superior effect for the prevention and treatment of cellular necrosis and necrosis-associated diseases, whereby they completed the present invention.

Therefore, it is an object of the present invention to provide a novel indole amide compound of Formula (1), a pharmaceutically acceptable salt or isomer thereof.

It is another object of the present invention to provide a composition for the prevention or treatment of cellular necrosis and necrosis-associated diseases, in particular, for hepatoprotection, hepatic functional improvement, and prevention or treatment of acute/chronic hepatic diseases, which comprises as an active ingredient the compound of Formula (1), a pharmaceutically acceptable salt or isomer thereof together with a pharmaceutically acceptable carrier or diluent.

It is still another object of the present invention to provide a method for the prevention or treatment of cellular necrosis and necrosis-associated diseases, in particular, for hepatoprotection, hepatic functional improvement, and prevention or treatment of acute/chronic hepatic diseases using said composition.

Solution to Problem

To accomplish the above objects, the present invention provides an indole amide compound of the following Formula (1) or a pharmaceutically acceptable salt or isomer thereof:

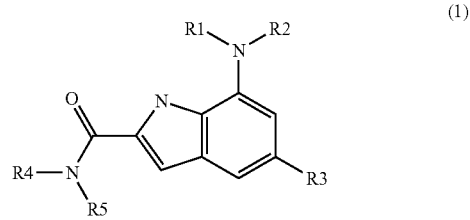

in which

R1 represents hydrogen, $C_1$-$C_6$-alkyl or —$(CH_2)_n$—$C_3$-$C_8$-cycloalkyl, n denotes a number of 0 to 2, R2 represents —X—$(CH_2)_n$-A-R6, wherein X represents a direct bond or —C(O)—, A represents a direct bond, or represents $C_3$-$C_8$-cycloalkyl or $C_6$-$C_{10}$ aryl, or represents 4- to 8-membered heterocyclyl or heteroaryl each of which has 1 to 3 heteroatoms selected from N, O and S, R6 represents hydrogen, $C_1$-$C_6$-alkyl, halogen, hydroxy, amino, nitrile, nitro or —$CO_2$—R7, and R7 represents hydrogen, $C_1$-$C_6$-alkyl, $C_6$-$C_{10}$ aryl or $C_6$-$C_{10}$ aryl-$C_1$-$C_6$-alkyl, or represents 5- or 6-membered heterocyclyl or heteroaryl each of which optionally contains oxo, and has 1 to 3 heteroatoms selected from N, O and S, R1 and R2 may together represent —$(CH2)_r$-, wherein r denotes a number of 4 to 6, R3 represents hydrogen, halogen, hydroxy, —O—R7, —NH—R7 or —$(CH_2)_m$—R7, wherein m denotes a number of 0 to 3, R4 represents —$(CHR7)_n$-B—(Z—R8)(Z'—R9), wherein B represents a direct bond, or represents $C_6$-$C_{10}$ aryl, or represents 4- to 9-membered heterocyclyl or heteroaryl each of which has 1 to 3 heteroatoms selected from N, O and S, Z and Z' independently of one another represent a direct bond, —$(CH_2)_m$—, —O— or —N—, and R8 and R9 independently of one another represent hydrogen, halogen, hydroxy, amino, di($C_1$-$C_6$-alkyl)amino, $C_1$-$C_6$-alkyl, —$CO_2$R7, $C_3$-$C_8$-cycloalkyl, $C_6$-$C_{10}$-aryl, $C_6$-$C_{10}$-aryloxy, $C_6$-$C_{10}$-aryl-$C_1$-$C_6$-alkyl or $C_6$-$C_{10}$-aryl-$C_1$-$C_6$-alkylamino, or represents 4- to 8-membered heterocyclyl which has 1 to 3 heteroatoms selected from N, O and S, R5 represents —$(CH_2)_m$—R10, wherein R10 represents hydrogen, $C_1$-$C_6$-alkyl or $C_6$-$C_{10}$-aryl, Z' and R5 may be connected with an atom(s) to which they are attached to form the structure

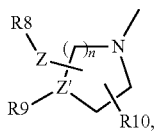

provided that when Z' is —O—, R9 does not exist, where alkyl, alkoxy, aryl, cycloalkyl, heterocycle and heteroaryl may be optionally substituted, and the substituents are one or more selected from the group consisting of hydroxy, halogen, nitrile, amino, alkylamino, dialkylamino, carboxy, alkyl, alkoxy, arylalkoxy and oxo.

In the above definitions for the compound of Formula (1), the term "alkyl" means an aliphatic hydrocarbon radical. Alkyl may be saturated alkyl that does not comprise alkenyl or alkynyl moiety, or unsaturated alkyl that comprises at least one alkenyl or alkynyl moiety. "Alkenyl" means a group containing at least one carbon-carbon double bond, and "alkynyl" means a group containing at least one carbon-carbon triple bond. Alkyl may be branched or straight-chain when used alone or in combination such as alkoxy.

Alkyl group may have 1 to 20 carbon atoms unless otherwise defined. Alkyl group may be a medium-sized alkyl having 1 to 10 carbon atoms. Otherwise, alkyl group may be a lower alkyl having 1 to 6 carbon atoms. Typical examples thereof include, but are not limited to, methyl, ethyl, propyl, isopropyl, n-butyl, isobutyl, t-butyl, pentyl, hexyl, ethenyl, propenyl, butenyl, etc. For example, $C_1$-$C_4$-alkyl has 1 to 4 carbon atoms in the alkyl chain, and is selected from the group consisting of methyl, ethyl, propyl, isopropyl, n-butyl, iso-butyl, sec-butyl and t-butyl.

The term "alkoxy" means an alkyloxy having 1 to 10 carbon atoms unless otherwise defined.

The term "cycloalkyl" means a saturated aliphatic 3- to 10-membered cycle unless otherwise defined. Typical examples thereof include, but are not limited to, cyclopropyl, cyclobutyl, cyclopentyl, cyclohexyl, etc.

The term "aryl" includes at least one ring having covalent π electron system—for example, monocyclic or fused polycyclic (i.e., cycles that share the adjacent carbon atom pairs) groups. In the present specification, aryl means an aromatic 4- to 10-membered, preferably 6- to 10-membered, monocyclic or multicyclic ring including phenyl, naphthyl, etc., unless otherwise defined.

The term "heteroaryl" means an aromatic 3- to 10-membered, preferably 4-to 8-membered, more preferably 5- or 6-membered cycle that has 1 to 4 heteroatoms selected from N, O and S, and may be fused with benzo or $C_3$-$C_8$ cycloalkyl, unless otherwise defined. The monocyclic heteroaryl includes, but is not limited to, thiazole, oxazole, thiophene, furan, pyrrole, imidazole, isoxazole, isothiazole, pyrazole, triazole, triazine, thiadiazole, tetrazole, oxadiazole, pyridine, pyridazine, pyrimidine, pyrazine and the like. The bicyclic heteroaryl includes, but is not limited to, indole, indoline, benzothiophene, benzofuran, benzimidazole, benzoxazole, benzisoxazole, benzthiazole, benzthiadiazole, benztriazole, quinoline, isoquinoline, purine, puropyridine and the like.

The term "heterocycle" means a 3- to 10-membered, preferably 4- to 8-membered, more preferably 5- or 6-membered cycle that has 1 to 4 heteroatoms selected from N, O and S, may be fused with benzo or $C_3$-$C_8$ cycloalkyl, and is saturated or contains 1 or 2 double bonds, unless otherwise defined. The heterocycle includes, but is not limited to, pyrroline, pyrrolidine, imidazoline, imidazolidine, pyrazoline, pyrazolidine, pyran, piperidine, morpholine, thiomorpholine, piperazine, hydrofuran and the like.

Other terms and abbreviations in the present specification may be understood to have the meaning conventionally used in this field by a person skilled in the art, unless otherwise defined.

According to a preferred embodiment of the present invention, in the compound of Formula (1):

R1 represents hydrogen, $C_1$-$C_6$-alkyl or —$(CH_2)_n$—$C_3$-$C_8$-cycloalkyl, n denotes a number of 0 to 2, R2 represents —X—$(CH_2)_n$-A-R6, wherein X represents a direct bond or —C(O)—, A represents a direct bond, or represents $C_4$-$C_8$-cycloalkyl or $C_6$-$C_{10}$ aryl, or represents 4- to 8-membered heterocyclyl or heteroaryl each of which has 1 to 3 heteroatoms selected from N, O and S, R6 represents hydrogen, $C_1$-$C_6$-alkyl, halogen, amino, nitrile or —$CO_2$—R7, and R7 represents hydrogen, $C_1$-$C_6$-alkyl, $C_6$-$C_{10}$ aryl or $C_6$-$C_{10}$ aryl-$C_1$-$C_6$-alkyl, or represents 5- or 6-membered heterocyclyl or heteroaryl each of which optionally contains oxo, and has 1 to 3 heteroatoms selected from N, O and S, R1 and R2 may together represent —$(CH_2)_r$—, wherein r denotes a number of 4 to 6, R3 represents hydrogen, halogen or $C_1$-$C_6$-alkyl, R4 represents —$(CHR7)_n$-B—(Z—R8)(Z'—R9), wherein B represents a direct bond, or represents phenyl, or represents 4- to 9-membered heterocyclyl or heteroaryl each of which has 1 to 3 heteroatoms selected from N, O and S, Z and Z' independently of one another represent a direct bond, —$(CH_2)_m$—, —O— or —N—, m denotes a number of 0 to 3, and R8 and R9 independently of one another represent hydrogen, halogen, hydroxy, amino, di($C_1$-$C_6$-alkyl)amino, $C_1$-$C_6$-alkyl optionally substituted with halogen, —$CO_2$R7, $C_4$-$C_6$-cycloalkyl, $C_6$-$C_{10}$-aryl optionally substituted with halogen or $C_1$-$C_6$-alkyl, $C_6$-$C_{10}$-aryloxy optionally substituted with halogen, $C_6$-$C_{10}$-aryl-$C_1$-$C_6$-alkyl or $C_6$-$C_{10}$-aryl-$C_1$-$C_6$-alkylamino optionally substituted with halogen or di($C_1$-$C_6$-alkyl)amino, or represents 4- to 8-membered heterocyclyl which has 1 to 3 heteroatoms selected from N, O and S, R5 represents —$(CH_2)_m$—R10, wherein R10 represents hydrogen, $C_1$-$C_6$-alkyl optionally substituted with amino or $C_6$-$C_{10}$-aryl optionally substituted with halogen, Z' and R5 may be connected with an atom(s) to which they are attached to form the structure

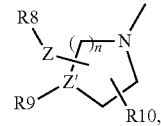

provided that when Z' is —O—, R9 does not exist.

In the compound of Formula (1) according to the present invention, Formula (1) may represent the following Formulas (1a) and (1b) depending on whether R5 and Z' are connected to form a ring or not:

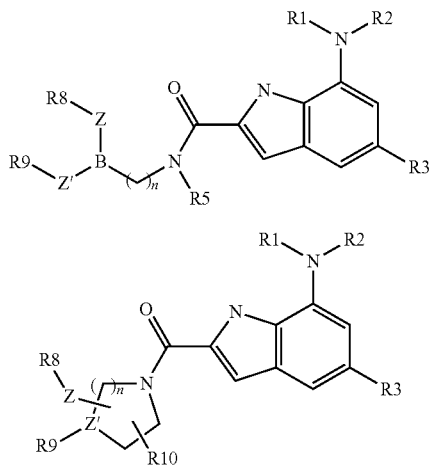

wherein R1, R2, R3, R5, R8, R9, R10, Z, Z', B and n are the same as defined above.

Substituent R1 more preferably represents hydrogen, isopentyl or cyclopentylmethyl.

Substituent R2 more preferably represents —X—$(CH_2)_n$-A-R6, wherein n denotes a number of 0 to 2, X represents a direct bond or —C(O)—, A represents a direct bond, or represents $C_3$-$C_6$-cycloalkyl or phenyl, or represents 4- to 6-membered heterocyclyl or heteroaryl each of which has 1 to 3 heteroatoms selected from N, O and S, and R6 represents hydrogen, $C_1$-$C_6$-alkyl, amino or —$CO_2H$. R2 most preferably represents cyclopentyl, piperidine, isopentyl, cyclopentylmethyl, phenethyl, pentyl, cyclopropylmethyl, 2-aminopyridin-3-ylmethyl, thiazolmethyl, pyrrolidine, pyrrolidin-2-ylmethyl, piperidin-3-yl, aminomethylcarbonyl, acetic acid, tetrahydropyran or cyclohexyl.

Substituents R1 and R2 together more preferably represent —$(CH_2)_5$—.

Substituent R3 more preferably represents hydrogen, halogen or $C_1$-$C_3$-alkyl. R3 most preferably represents chloro, bromo or methyl.

In substituent R4, B more preferably represents a direct bond, or represents phenyl, pyrrolidine, morpholine, thiazole or indazole.

In substituent R4, Z and Z' independently of one another more preferably represent —$(CH_2)_m$—, —O— or —N—.

In substituent R4, R8 more preferably represents hydrogen, halogen, hydroxy, amino, di($C_1$-$C_6$-alkyl)amino, $C_1$-$C_6$-alkyl optionally substituted with halogen, —$CO_2R7$ (R7 represents hydrogen or $C_1$-$C_3$-alkyl), $C_4$-$C_6$-cycloalkyl, phenyl optionally substituted with halogen or $C_1$-$C_3$-alkyl, phenoxy optionally substituted with halogen, phenyl-$C_1$-$C_3$-alkyl or benzylamino optionally substituted with halogen or di($C_1$-$C_3$-alkyl)amino, or represents 5- or 6-membered heterocyclyl which has 1 or 2 heteroatoms selected from N, O and S. R8 most preferably represents dimethylamino, amino, isopentyl, fluoro, 3,5-dimethyl-phenyl, difluoromethyl, phenyl, benzyl, isopropyl, cyclopentyl, phenoxy, 3,4-difluorophenoxy, 3-dimethylamino-benzylamino, 3,5-difluorobenzylamino, hydroxy, carboxy, piperidine, methoxycarbonyl or pyrrolidine.

In substituent R4, R9 more preferably represents hydrogen, phenoxy or benzyl.

In substituent R5, R10 more preferably represents hydrogen, 2,4-difluorophenyl, 4-fluorophenyl or aminomethyl.

Typical compounds of the compound of Formula (1) according to the present invention include the following:
5-Chloro-7-cyclopentylamino-1H-indol-2-carboxylic acid (4-phenoxy-phenyl)-amide;
5-Chloro-7-(pyrrolidin-3-ylamino)-1H-indol-2-carboxylic acid (4-phenoxy-phenyl)-amide;
5-Chloro-7-(piperidin-4-ylamino)-1H-indol-2-carboxylic acid [4-(3,4-difluoro-phenoxy)-phenyl]-amide;
5-Chloro-7-(piperidin-4-ylamino)-1H-indol-2-carboxylic acid (3-phenoxy-phenyl)-amide;
5-Chloro-7-[(pyrrolidin-2-ylmethyl)-amino]-1H-indol-2-carboxylic acid benzylamide;
5-Chloro-7-(piperidin-3-ylamino)-1H-indol-2-carboxylic acid (4-phenoxy-phenyl)-amide;
5-Chloro-7-(piperidin-4-ylamino)-1H-indol-2-carboxylic acid (4-phenoxy-phenyl)-amide;
5-Chloro-7-[(pyrrolidin-2-ylmethyl)-amino]-1H-indol-2-carboxylic acid (3-phenoxy-phenyl)-amide;
5-Chloro-7-[(pyrrolidin-2-ylmethyl)-amino]-1H-indol-2-carboxylic acid (3-cyclopentyloxy-5-phenoxy-phenyl)-amide;
5-Chloro-7-[(pyrrolidin-2-ylmethyl)-amino]-1H-indol-2-carboxylic acid (4-phenoxy-phenyl)-amide;
7-[(2-Amino-pyridin-3-ylmethyl)-amino]-5-chloro-1H-indol-2-carboxylic acid [4-(3,4-difluoro-phenoxy)-phenyl]-amide;
5-Chloro-7-(piperidin-4-ylamino)-1H-indol-2-carboxylic acid (3-cyclopentyloxy-phenyl)-amide;
5-Chloro-7-(piperidin-4-ylamino)-1H-indol-2-carboxylic acid (3-morpholin-4-ylmethyl-phenyl)-amide;
5-Chloro-7-(piperidin-4-ylamino)-1H-indol-2-carboxylic acid biphenyl-3-ylamide;
5-Chloro-7-(piperidin-4-ylamino)-1H-indol-2-carboxylic acid (3-benzyloxy-phenyl)-amide;
5-Chloro-7-(piperidin-4-ylamino)-1H-indol-2-carboxylic acid (4-trifluoromethoxy-phenyl)-amide;
5-Chloro-7-(piperidin-4-ylamino)-1H-indol-2-carboxylic acid [4-(3,5-dimethyl-phenoxy)-phenyl]-amide;
5-Chloro-7-(piperidin-4-ylamino)-1H-indol-2-carboxylic acid [2-(3-fluoro-phenyl)-ethyl]-amide;
5-Chloro-7-[(thiazol-2-ylmethyl)-amino]1H-indol-2-carboxylic acid (3-phenoxy-phenyl)-amide;
5-Chloro-7-(piperidin-4-ylamino)-1H-indol-2-carboxylic acid (4-isopentyloxy-phenyl)-amide;
5-Chloro-7-[(pyrrolidin-2-ylmethyl)-amino]-1H-indol-2-carboxylic acid [4-(3,4-dimethyl-phenoxy)-phenyl]-amide;
(5-Chloro-7-cyclopentylamino-1H-indol-2-yl)-pyrrolidin-1-yl-methanone;
(R)-1-(5-chloro-7-cyclopentylamino-1H-indol-2-carbonyl)-pyrrolidin-3-carboxylic acid methyl ester;
(S)-1-(5-chloro-7-cyclopentylmethylamino-1H-indol-2-carbonyl)-pyrrolidin-3-carboxylic acid methyl ester;
(R)-1-[5-chloro-7-(tetrahydro-pyran-4-ylamino)-1H-indol-2-carbonyl]-pyrrolidin-3-carboxylic acid methyl ester;
(S)-1-[5-methyl-7-(tetrahydro-pyran-4-ylamino)-1H-indol-2-carbonyl]-pyrrolidin-3-carboxylic acid methyl ester;
(5-Bromo-7-cyclohexylamino-1H-indol-2-yl)-morpholin-4-yl-methanone;
(7-Cyclopentylamino-5-methyl-1H-indol-2-yl)-morpholin-4-yl-methanone;
(7-Cyclopentylamino-5-methyl-1H-indol-2-yl)-piperazin-4-yl-methanone;
5-Chloro-7-cyclopentylamino-1H-indol-2-carboxylic acid (1-benzyl-pyrrolidin-3-ylmethyl)-amide;

7-Cyclopentylamino-5-methyl-1H-indol-2-carboxylic acid (2-dimethylamino-ethyl)-amide;
7-Cyclopentylamino-5-methyl-1H-indol-2-carboxylic acid (2-morpholin-4-yl-ethyl)-amide;
(4-Benzyl-piperazin-1-yl)-[5-chloro-7-(piperidin-4-ylamino)-1H-indol-2-yl]-methanone;
[5-Chloro-7-(piperidin-4-ylamino)-1H-indol-2-yl]-[(R)-3-(3,4-difluoro-phenoxymethyl)-pyrrolidin-1-yl]-methanone;
[5-Chloro-7-(piperidin-4-ylamino)-1H-indol-2-yl]-((R)-3-phenoxymethyl-pyrrolidin-1-yl]-methanone;
(R)-1-[5-chloro-7-(tetrahydro-pyran-4-ylamino)-1H-indol-2-carbonyl]-pyrrolidin-3-carboxylic acid;
[5-Chloro-7-(tetrahydropyran-4-ylamino)-1H-indol-2-yl]-((R)-3-hydroxymethyl-pyrrolidin-1-yl)-methanone;
(S)-1-[5-methyl-7-(tetrahydropyran-4-ylamino)-1H-indol-2-carbonyl]-pyrrolidin-3-carboxylic acid;
7-(2-Amino-acetylamino)-5-chloro-1H-indol-2-carboxylic acid (4-phenoxy-phenyl)-amide;
(3-Aminomethyl-pyrrolidin-1-yl)-(5-chloro-7-cyclopentylamino-1H-indol-2-yl)-methanone;
(5-Chloro-7-cyclopentylamino-1H-indol-2-yl)-(3-piperidin-1-ylmethyl-pyrrolidin-1-yl)-methanone;
[5-Chloro-7-(tetrahydro-pyran-4-ylamino)-1H-indol-2-yl]-(3-piperidin-1-ylmethyl-pyrrolidin-1-yl)-methanone;
(3-Aminomethyl-pyrrolidin-1-yl)-[5-chloro-7-(tetrahydropyran-4-ylamino)-1H-indol-2-yl]-methanone;
((R)-3-amino-pyrrolidin-1-yl)-(5-chloro-7-cyclopentylamino-1H-indol-2-yl)-methanone;
(5-Chloro-7-cyclopentylamino-1H-indol-2-yl)-{3-[(3-dimethylamino-benzylamino)-methyl]-pyrrolidin-1-yl}-methanone;
(3-Aminomethyl-pyrrolidin-1-yl)-[5-chloro-7-(3-methyl-butylamino)-1H-indol-2-yl]-methanone;
(3-Aminomethyl-pyrrolidin-1-yl)-[5-chloro-7-(cyclopentylmethyl-amino)-1H-indol-2-yl]-methanone;
(3-Aminomethyl-pyrrolidin-1-yl)-(5-chloro-7-piperidin-1-yl-1H-indol-2-yl]-methanone;
(3-Aminomethyl-pyrrolidin-1-yl)-(5-chloro-7-penethylamino-1H-indol-2-yl]-methanone;
(3-Aminomethyl-pyrrolidin-1-yl)-(5-chloro-7-pentylamino-1H-indol-2-yl]-methanone;
(3-Aminomethyl-pyrrolidin-1-yl-(5-chloro-7-cyclohexylamino-1H-indol-2-yl]-methanone;
(3-Aminomethyl-piperidin-1-yl)-(5-chlor)-7-cyclopentylamino-1H-indol-2-yl]-methanone;
(3-Aminomethyl-pyrrolidin-1-yl)-[7-(bis-cyclopropylmethyl-amino)-5-chloro-1H-indol-2-yl]-methanone;
(3-Aminomethyl-pyrrolidin-1-yl)-{7-[bis-(3-methyl-butyl)-amino]-5-chloro-1H-indol-2-yl}-methanone;
((S)-3-amino-pyrrolidin-1-yl)-(5-chloro-7-cyclopentylamino-1H-indol-2-yl}-methanone;
{7-[Bis-(3-methyl-butyl)-amino]-5-chloro-1H-indol-2-yl}-[3-(4-fluoro-benzylaminomethyl)-pyrrolidin-1-yl]-methanone;
{7-[Bis-(3-methyl-butyl)-amino]-5-chloro-1H-indol-2-yl}-[3-(3,4-difluoro-benzylaminomethyl)-pyrrolidin-1-yl]-methanone;
(3-Aminomethyl-pyrrolidin-1-yl)-(5-bromo-7-cyclopentylamino-1H-indol-2-yl)-methanone;
7-Cyclopentylamino-5-methyl-1H-indol-2-carboxylic acid (pyrrolidin-3-ylmethyl)-amide;
{7-[Bis-(3-methyl-butyl)-amino]-5-chloro-1H-indol-2-yl}-[(3R,4R)-3-(2,4-difluoro-phenyl)-4-pyrrolidin-1-ylmethyl-pyrrolidin-1-yl]-methanone;
{7-[Bis-(3-methyl-butyl)-amino]-5-chloro-1H-indol-2-yl}-[(3R,4R)-3-(4-chloro-phenyl)-4-pyrrolidin-1-ylmethyl-pyrrolidin-1-yl]-methanone;
(5-Chloro-7-cyclopentylamino-1H-indol-2-yl}-[(3R,4R)-3-(2,4-difluoro-phenyl)-4-pyrrolidin-1-ylmethyl-pyrrolidin-1-yl]-methanone;
(5-Chloro-7-(tetrahydropyran-4-ylamino)-1H-indol-2-yl)-[(3R,4R)-3-(2,4-di fluoro-phenyl)-4-pyrrolidin-1-ylmethyl-pyrrolidin-1-yl]-methanone;
(5-Chloro-7-(piperidin-4-ylamino)-1H-indol-2-yl}-[(3R,4R)-3-(2,4-difluoro-phenyl)-4-pyrrolidin-1-ylmethyl-pyrrolidin-1-yl]-methanone;
(5-Chloro-7-cyclopentylamino)-1H-indol-2-carboxylic acid ((R)-2-phenyl-1-pyrrolidin-1-ylmethyl-ethyl)-amide;
[5-Methyl-2-(pyrrolidin-1-carbonyl)-1H-indol-7-ylamino]-acetic acid; and
[7-Cyclopentylamino-5-(1,1-dioxo-thiomorpholin-4-ylmethyl)-1H-indol-2-yl]-pyrrolidin-1-yl-methanone.

The compound of Formula (1) according to the present invention can also form a pharmaceutically acceptable salt. Such a "pharmaceutically acceptable salt" includes non-toxic acid addition salt containing pharmaceutically acceptable anion—for example, a salt with inorganic acids such as hydrochloric acid, sulfuric acid, nitric acid, phosphoric acid, hydrobromic acid, hydriodic acid, etc.; a salt with organic carboxylic acids such as tartaric acid, formic acid, citric acid, acetic acid, trichloroacetic acid, trifluoroacetic acid, gluconic acid, benzoic acid, lactic acid, fumaric acid, maleic acid, salicylic acid, etc.; or a salt with sulfonic acids such as methanesulfonic acid, ethanesulfonic acid, benzenesulfonic acid, p-toluenesulfonic acid, naphthalenesulfonic acid, etc. The compound of Formula (1) can also form a pharmaceutically acceptable base addition salt—for example, a salt with alkali metals or alkaline earth metals such as lithium, sodium, potassium, calcium, magnesium, etc.; a salt with amino acids such as lysine, arginine, guanidine, etc.; or an organic salt with dicyclohexylamine, N-methyl-D-glucamine, tris(hydroxymethyl)methylamine, diethanolamine, choline, triethylamine, etc. The compound of Formula (1) of the present invention may be converted to their salts according to any of the conventional methods, and the salt formation could be easily carried out by a person skilled in the art based on the structure of Formula (1) without additional explanations thereon.

On the other hand, the compound of Formula (1) of the present invention may have an asymmetric carbon center(s) in the structure, and so may exist in the form of an R or S isomer, a racemate, a mixture of diastereomers, or an individual diastereomer. All such isomers are also included in the scope of the present invention.

The present invention also provides processes for preparing the compound of Formula (1). Hereinafter, the processes for preparing the compound of Formula (1) are illustrated by exemplary reaction schemes for the purpose of better understanding. However, a skilled artisan in the field to which the present invention pertains could prepare the compound of Formula (1) via various routes according to their structures, and such processes should be construed to fall under the scope of the present invention. In other words, the compound of Formula (1) may be prepared by optionally combining various synthetic methods which are described in the present specification or disclosed in the prior arts. The processes for preparing the compound of Formula (1) cover even such processes, and are not limited to those explained below.

First of all, the compound of Formula (1) may be prepared according to the following Reaction Scheme 1 by reducing the nitro group of the compound (2) to prepare the amine compound (3), and by carrying out reductive amination on the formed amine group with compound (4).

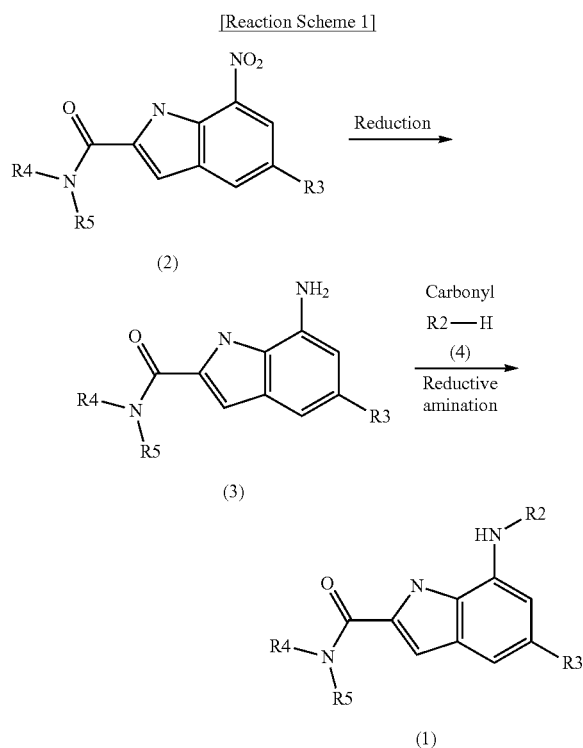

In the above Reaction Scheme 1,
R2, R3, R4 and R5 are the same as defined above.

Compound (3) may be prepared by reducing compound (2). The reduction may be carried out by the use of an acid catalyst and a metal, or a metallic catalyst in the presence of hydrogen gas.

An acid used in the reduction using an acid catalyst and a metal is, for example, inorganic acid such as hydrochloric acid, sulfuric acid, nitric acid, phosphoric acid, etc.; organic carboxylic acid such as acetic acid, trifluoroacetic acid, etc.; or salt of amine acid such as ammonium chloride, etc., and preferably hydrochloric acid, acetic acid or ammonium chloride. An acid is conventionally used in an amount of 0.01-10 equivalents based on 1 equivalent of compound (2), and preferably 0.1-5 equivalents. A metal used in the reduction is, for example, iron, zinc, lithium, sodium, or tin (usually, tin chloride), and preferably iron, zinc or tin chloride. A metal is conventionally used in an amount of 1-20 equivalents based on 1 equivalent of compound (2), and preferably 1-10 equivalents. The reaction using a metal in the presence of an acid catalyst may be carried out in an inert solvent. An inert solvent is—for example, alkyl alcohol such as methanol, ethanol, etc.; ether such as tetrahydrofuran, diethyl ether, etc., or alkyl ester such as ethyl acetate, etc., and preferably methanol, ethanol, tetrahydrofuran or ethyl acetate. The reaction temperature is conventionally −10-200° C., and preferably 25-120° C. The reaction time is conventionally 10 minutes-60 hours, and preferably 10 minutes-12 hours.

A metallic catalyst used in the reaction using a metallic catalyst in the presence of hydrogen gas is, for example, palladium, nickel, platinum, ruthenium, rhodium, etc., and preferably palladium or nickel. A metallic catalyst is conventionally used in an amount of 0.001-2 equivalents based on 1 equivalent of compound (2), and preferably 0.01-1 equivalent. The pressure of hydrogen gas is conventionally 1-10 atm, and preferably 1-3 atm. This reaction may be carried out in an inert solvent—for example, alkyl alcohol such as methanol, ethanol, etc.; ether such as tetrahydrofuran, diethyl ether, etc.; or alkyl acetate such as methyl acetate, ethyl acetate, etc., and preferably methanol, ethanol or ethyl acetate. The temperature of the reaction using a metallic catalyst is conventionally −10-200° C., and preferably 25-50° C. The reaction time is conventionally 10 minutes-60 hours, and preferably 10 minutes-12 hours.

Compound (4) may be prepared via reductive amination on the amine group of compound (3).

Reductive amination may be carried out via the reaction with aldehyde or ketone using a reducing agent, and an acid catalyst may be used if necessary. The amount of aldehyde or ketone is conventionally 1-10 equivalents based on 1 equivalent of compound (3), and preferably 1-3 equivalents. A reducing agent used in the reaction may be sodium borohydride, sodium cyanoborohydride (NaBH$_3$CN), sodium triacetoxyborohydride (NaBH[OAc]$_3$), etc. A reducing agent is conventionally used in an amount of 1-10 equivalents based on 1 equivalent of compound (3), and preferably 1-3 equivalents. An acid catalyst used in the reaction is, for example, inorganic acid such as hydrochloric acid, sulfuric acid, nitric acid, phosphoric acid, etc.; organic carboxylic acid such as acetic acid, trifluoroacetic acid, etc.; or salt of amine acid such as ammonium chloride, etc., and preferably hydrochloric acid or acetic acid. An acid is conventionally used in an amount of 0.1-10 equivalents based on 1 equivalent of compound (3), and preferably 1-5 equivalents. This reaction may be carried out in an inert solvent—for example, ether such as tetrahydrofuran, diethyl ether, etc.; or chloroalkane such as dichloromethane, chloroform, dichloroethane, etc., and preferably dichloroethane or chloroform. The temperature of the reaction is conventionally −10-100° C., and preferably −10-50° C. The reaction time is conventionally 10 minutes-60 hours, and preferably 10 minutes-12 hours.

Compound (2) may be prepared by the amidation of compound (5) and compound (6) as the following Reaction Scheme 2.

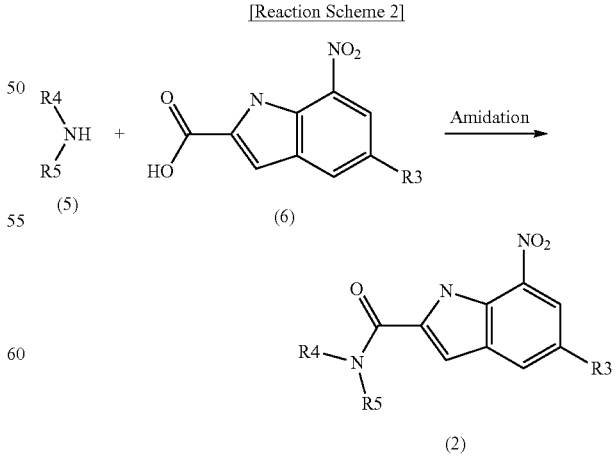

In the above Reaction Scheme 2,
R3, R4 and R5 are the same as defined above.

Examples of known coupling agents used in amide coupling include, but are not limited to, a mixture of carboimide such as dicyclohexylcarbodiimide (DCC), 1-(3-dimethylaminopropyl)-3-ethylcarbodiimide (EDC), 1,1'-dicarbonyldiimidazole (CDI), etc. with 1-hydroxy-benzotriazole (HOBT) or 1-hydroxy-7-azabenzotriazole (HOAT), or bis-(2-oxo-3-oxazolidinyl)-phosphinic acid chloride (BOP-Cl), diphenylphosphoryl azide (DPPA), N-[dimethylamino-1H-1,2,3-triazol [4,5-b]pyridine-1-ylmethylene]-N-methyl methane aminium (HATU), etc. A coupling agent is conventionally used in an amount of 1-10 equivalents based on 1 equivalent of compound (5), and preferably 1-3 equivalents. HOBT or HOAT is conventionally used in an amount of 1-10 equivalents based on 1 equivalent of compound (5), and preferably 1-3 equivalents. When hydrochloric acid salt of amine is used in coupling reaction, an acid should be removed by the use of a base. The base used at this time is an organic base such as triethylamine or diisopropylethylamine. The base is conventionally used in an amount of 1-10 equivalents based on 1 equivalent of compound (5), and preferably 1-3 equivalents. The coupling reaction may be carried out in an inert solvent such as tetrahydrofuran, diethylether or N,N-dimethylformamide. The temperature of the reaction is conventionally −10-200° C., and preferably 25-120° C. The reaction time is conventionally 10 minutes-60 hours, and preferably 10 minutes-12 hours.

7-Nitroindole compound (6) is commercially available or may be synthesized according to the following Reaction Scheme 3.

documents (Heterocycles, 68[11], 2285-2299, 2006, or Bioorganic & Medicinal Chemistry Letters, 14[19], 4903-4906, 2004).

Hydrazine compound (8) is also commercially available, or may be prepared by modifying the amine group of compound (7) to hydrazine group according to the method disclosed in the document (Journal of the America Chemical Society, 198[48], 15374-15375, 2006).

Hydrazone compound (10) may be obtained by combining ketone compound (9) with hydrazine compound (8). A base is not used when hydrazine compound (8) is a neutral form, but should be used when the compound is an acidic salt form to make it to a neutral form. As the base, metal hydroxides such as sodium hydroxide, lithium hydroxide, etc., metal carbonates such as sodium bicarbonate, potassium carbonate, etc., metal acetates such as sodium acetate, etc., organic bases such as triethylamine, pyridine, etc., preferably sodium acetate, sodium bicarbonate, etc., may be used.

On the other hand, hydrazone compound (10) may be prepared by reacting diazonium salt with ketone compound (11) in the presence of a base according to Japp-Klingemann rearrangement method disclosed in the document (Organic Process Research & Development, 2, 1988, 214-220).

The cyclization reaction of compound (10) may be carried out according to the method disclosed in the documents (Journal of Organic Chemistry, 68[24], 2003, 9506-9509; Tetrahedron, 55[34], 1999, 10271-10282; etc). The acid that can be used in this reaction may be polyphosphoric acid,

[Reaction Scheme 3]

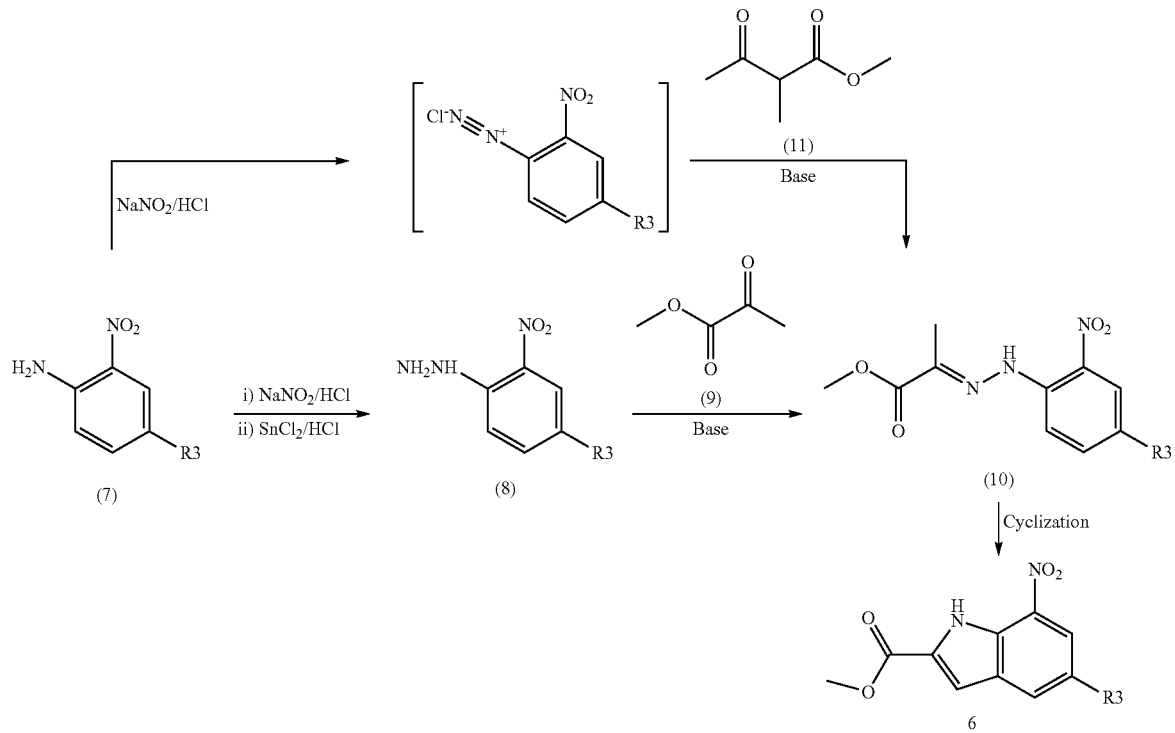

In the above Reaction Scheme 3, R3 is the same as defined above.

Nitro-aniline compound (7) is commercially available or may be prepared according to the method disclosed in the hydrochloric acid, p-toluenesulfonic acid, sulfuric acid, acetic acid, etc. In the case of polyphosphoric acid, it may be used alone or in combination with aromatic hydrocarbon such as benzene, toluene, etc.

The compounds whose preparation methods are not specifically explained in the present specification are known per se, or those that can be prepared from a known compound according to a known process or a similar process thereto.

In the processes according to the present invention, mixtures are conventionally separated by column chromatography. In the case of a final product, it can be separated after completion of reaction by recrystallization or normal or reverse-phased HPLC (Waters, Delta Pack, 300×50 mm I.D., C18 5 μm, 100 A). When the product is purified by recrystallization or HPLC, the compound may be obtained in the form of a salt with trifluoroacetic acid. When a hydrochloric acid salt is desirable, ion exchange resin can be used.

As explained above, the compounds according to the present invention, starting materials, intermediates, etc. for the preparation thereof may be obtained by various processes, and such processes for preparing the compound of Formula (1) should be construed to fall under the scope of the present invention.

The present invention further provides a composition for the prevention or treatment of necrosis and associated diseases, which comprises a therapeutically effective amount of the compound of Formula (1), a pharmaceutically acceptable salt or isomer thereof as an active ingredient together with a pharmaceutically acceptable carrier or diluent.

In addition, the present invention provides a method for the prevention or treatment of necrosis and associated diseases using the above composition.

Necrosis and associated diseases which can be treated and/or prevented according to the present invention include acute/chronic hepatic disease (e.g., hepatitis, hepatic fibrosis, hepatocirrhosis), neurodegenerative disease (e.g., dementia, Parkinson's disease, Huntington's disease), ischemic cardiac disease, reperfusion injury, ischemic stroke or ischemic injury, pancreatitis, bacterial/viral sepsis, diabetes mellitus or diabetic complications, diabetic vascular disease (in particular, these diabetes are caused by pancreatic cell destroying substances, and mediated by virus, hyperglycemia, fatty acid, diet, toxin, streptozotocin and the like), necrotizing procolitis, cystic fibrosis, rheumatoid arthritis, degenerative arthritis, nephropathy, bacterial infection, viral infection (e.g., HIV), multiple sclerosis, leukemia, lymphoma, neonatal respiratory distress syndrome, asphyxia, tuberculosis, endometriosis, angiasthenia, psoriasis, chilblain, steroid treatment complications, gangrene, pressure sores, hemoglobinuria, burns, hyperthermia, Crohn's disease, celiac disease, compartment syndrome, spinal cord injury, glomerulonephritis, muscular dystrophy, metabolic inherited disease, mycoplasmal disease, anthrax, Andersen's disease, congenital mitochondrial disease, phenylketonuria, placental infarction, syphilis, aseptic necrosis etc. In addition, necrosis and associated diseases caused by drugs and toxic substances are selected from the group consisting of the necrosis associated with alcoholism, the exposure to, and/or administration and/or self-administration of, cocaine, drugs (e.g., paracetamol), antibiotics, anti-cancer agent, adriamycin, puromycin, bleomycin, NSAID, cyclosporine, chemical toxins (e.g., carbon tetrachloride, cyanide, methanol, ethylene glycol), poison gas, agrochemicals, heavy metals (e.g., lead, mercury, cadmium), or injury due to the exposure to radioactivity/UV and associated necrosis thereof.

Specifically, the composition according to the present invention exhibits not only the effects for hepatoprotection and hepatic functional improvement, but also shows the prophylactic and therapeutic effects on chronic hepatic diseases such as fatty liver, hepatic fibrosis, hepatocirrhosis, etc. and acute/chronic hepatic disease such as hepatitis, etc. caused by virus or drugs. Consequently, complications of hepatic disease including, but not limited to, portal hypertention also may be prevented or treated. More particularly, the medical composition according to the present invention is also effective for the treatment or prevention of hepatic diseases selected from liver transplantation, alcoholic or non-alcoholic fatty liver, hepatic fibrosis, hepatocirrhosis and hepatitis caused by virus or drugs, and is effective for alcoholic acute/chronic hepatic disease.

Furthermore, the composition according to the present invention is effective for the treatment or prevention of fatty acid-induced fatty liver or acute/chronic hepatic disease derived from fatty liver.

As used herein, "treatment" means the interruption or delay of the progress of the disease when applied to a subject showing the onset of disease symptoms, and "prevention" means the interruption or delay of the sign of the onset of disease when applied to a subject who does not show, but is at risk of, the onset of disease symptoms.

The above-mentioned "pharmaceutical composition" may comprise pharmaceutically acceptable carriers, diluents, excipients, or their combinations, if needed, together with the compounds of the present invention. A pharmaceutical composition facilitates the administration of the compound into a living organism. There exist a number of techniques to administer the compound, and they include, but are not limited to, oral, injectable, aerosol, parenteral and topical administration.

As used herein, "carrier" means a substance which facilitates the incorporation of the compound into the cells or tissues. For example, dimethyl sulfoxide (DMSO) is a typical carrier which is used to facilitate the introduction of various organic compounds into the cells or tissues of living organisms.

As used herein, "diluent" is defined as a substance that is diluted in water which dissolves the compound, as well as stabilizes the biologically active form of the subject compound. The salts dissolved in buffer solution are utilized as diluents in the art. A typically used buffer solution is phosphate-buffered saline which mimics the salt form of human solution. Buffer diluents rarely alter the biological activities of the compound, as the buffer salts can control the pH of solution at low concentration.

As used herein, "pharmaceutically acceptable" means the property that does not impair the biological activities and physical properties of the compound.

The compound of the present invention can be formulated as various pharmaceutical dosage forms according to the desired purpose. For the preparation of the pharmaceutical composition of the present invention, active ingredient, specifically, the compound of Formula (1), a pharmaceutically acceptable salt or isomer thereof is mixed together with various pharmaceutically acceptable carriers which can be selected according to the formulation to be prepared. For example, the pharmaceutical composition of the present invention can be formulated as injectable preparation, oral preparation, etc., according to the desired purpose.

The compound of the present invention can be formulated by the methods known in the art, which utilize pharmaceutical carriers and excipients known in the art, and can be incorporated into containers of unit dose form or multi-dose form. The form of the preparation can be solutions, suspensions or emulsions in oily or aqueous media, and contain typical dispersing agents, suspending agents or stabilizers. Furthermore, for example, it can be a form of dry powder which is intended to be reconstructed by dissolving in sterile, pyrogen-free water prior to use. The compound of the present invention also can be formulated into suppository forms utilizing typical suppository base such as cocoa butter or other glycerides. As solid dosage forms for oral administration, capsules, tablets, pills, powder and granules can be prepared, and capsules and tablets are especially useful. Preferably, tablets and pills are prepared as enteric coated forms. Solid dosage forms can be prepared by mixing the compounds of the present invention together with carriers such as one or more inert diluents such as sucrose, lactose, starch, etc., lubricants such as magnesium stearate, disintegrants, binders, etc.

If needed, the compound of the present invention or the pharmaceutical composition containing the same can also be administered in combination with other active agents including cytoprotective agents with various action mechanisms of different types, especially the existing agents utilized for hepatoprotection, hepatic functional improvement, and prevention or treatment of hepatic disease—hepatocyte regeneration promoters, hepatic functional adjuvants, anti-viral agents, immunosuppressants, fibrosis inhibitors, etc.

The compound of the present invention or the pharmaceutical composition containing the same can be co-administered with a prophylactic or therapeutic agent for any drug-induced necrosis and associated diseases. These drugs include those for any disease group, such as antibiotics, anti-cancer agents, anti-viral agents, anti-infectives, anti-inflammatory agents, anti-coagulants, lipid-improving agents, cell death inhibitors, anti-hypertensive agents, anti-diabetic/anti-obesity agents, therapeutic agents for cardiovascular disease, therapeutic agents for neurodegenerative disease, anti-aging agents, therapeutic agents for metabolic disease, etc.

The compound of the present invention or the pharmaceutical composition containing the same can be used for the prevention of cell injury and subsequent necrosis and associated diseases derived by various causes such as toxins, and these causes include reactive oxygen species (ROS), heavy metals, alcohol, food, supplements, radiation, diet, etc.

The dosage of the compound of Formula (1) depends on the prescription of a physician, taking into account such factors as body weight, sex, age, condition of health, and diet of the patient, specific nature of the disease, administration time of the agent, administration method, mixing ratio of agents, and severity of the disease, etc. However, dosage needed for the treatment of an adult is typically from about 1.0 mg to 2,000 mg per day, depending on the intensity and frequency of the administration. When administered to an adult via intramuscular or intravenous routes, total dosage typically from about 1.0 mg to 300 mg per day will be sufficient when separately administered in a single dosage, but for some patients a higher daily dosage may be desirable.

The present invention further provides a method of preparing the composition for the prevention or treatment of necrosis and associated diseases, which comprises the step of mixing the compound of Formula (1), a pharmaceutically acceptable salt or isomer thereof as an active ingredient together with a pharmaceutically acceptable carrier or diluent.

The pharmaceutical composition according to the present invention can show hepatoprotection and hepatic functional improvement, and can prevent or treat acute/chronic hepatic diseases and complications of hepatic disease such as portal hypertension, but is not limited thereto.

Advantageous Effects of the Invention

A novel compound according to the present invention not only exhibits the effects for hepatoprotection and hepatic functional improvement, but also can be used in the prevention or treatment of chronic hepatic diseases such as fatty liver, hepatic fibrosis, hepatocirrhosis, etc. and acute/chronic hepatic diseases such as hepatitis, etc. caused by virus or drugs. In addition, the compound of the present invention shows necrosis inhibitory efficacy in cells from the pancreas, kidney, brain, cartilage, and heart.

Therefore, the compound of the present invention can be useful in the prevention and treatment of necrosis and associated diseases.

MODE FOR THE INVENTION

Hereinafter, the present invention is explained in more detail with the following examples. However, it must be understood that the protection scope of the present invention is not limited to the examples. In the following Preparation Examples and Examples, M means molar concentration, and N means normal concentration.

The abbreviations used in the following Preparation Examples and Examples are as follows:
Ac: acetyl
BOC: t-butoxycarbonyl
Bu: butyl
Bn: benzyl
c-Pen: cyclopentyl
c-Hex: cyclohexyl
DCM: dichloromethane
DIPEA: diisopropylethylamine
DMAP: 4-dimethylaminopyridine
DMF: N,N-dimethylformamide
EDC: 1-(3-dimethylaminopropyl)-3-ethylcarbodiimide, hydrochloride
Hex: n-hexane
HOBT: hydroxybenzotriazole
HBTU: 2-(1H-benzotriazol-1-yl)-1,1,3,3-tetramethyluronium hexafluorophosphate
i-Pr: isopropyl
i-Pen: isopentyl
KHMDS: potassium bis(trimethylsilyl)amide
Me: methyl
Ph: phenyl
PMB: para-methoxybenzyl
TEA: triethylamine
TFA: trifluoroacetic acid
THF: tetrahydrofuran
THP: tetrahydropyran
TMS: trimethylsilyl

PREPARATION EXAMPLE 1

5-Chloro-7-nitro-1H-indol-2-carboxylic acid

Step A: (4-Chloro-2-nitro-phenyl) hydrazine hydrochloride

Commercially available 4-chloro-2-nitroaniline (40 g, 0.23 mol) was dissolved in 12N hydrochloric acid (100 mL), and then sodium nitrite (16 g, 0.23 mol) dissolved in water (50 mL) was slowly added dropwise thereto at 0° C. The resulting mixture was stirred at 0° C. to room temperature for 30 minutes. After cooling the reactant to 0° C., tin(II) chloride (132 g, 0.70 mol) dissolved in 12 N hydrochloric acid (100 mL) was slowly added dropwise thereto, and then the mixture was stirred at 0° C. to room temperature for 3 hours. The obtained yellow solid was filtered, washed with a small amount of 6 N HCl, and dried to give the title compound (30 g, Yield 63%).

¹H-NMR (400 HMz, DMSO-d₆); δ 9.21 (s, 1H), 7.98 (d, J=2.4 Hz, 1H), 7.66 (d, J=9.6 Hz, 1H), 7.55 (dd, J=2.4, 9.6 Hz, 1H), 4.74 (br s, 2H)

Step B: 2-[(4-Chloro-2-nitro-phenyl)hydrazono]propionic acid methyl ester (4-Chloro-2-nitro-phenyl)hydrazine hydrochloride (30 g, 0.14 mol) obtained in Step A and methyl pyruvate (14.4 mL, 0.16 mol) were dissolved in methanol (300 mL), and then sodium acetate (14.2 g, 0.17 mol) was added thereto. The reaction solution was stirred at room temperature for 8 hours. The obtained yellow solid was filtered, washed with water and methanol, and then dried to give the title compound (30 g, Yield 82%).
¹H-NMR (400 HMz, CDCl₃); δ 10.88 (s, 1H), 8.21 (d, J=2.4 Hz, 1H), 8.01 (d, J=9.2 Hz, 1H), 7.56 (dd, J=2.4, 9.2 Hz, 1H), 3.90 (s, 3H), 2.23 (s, 3H).

Step C: 5-Chloro-7-nitro-1H-indol-2-carboxylic acid methyl ester

Polyphosphoric acid (100 mL) was added to 2-[(4-chloro-2-nitro-phenyl) hydrazono]propionic acid methyl ester (13 g, 46 mmol) obtained in Step B, and the mixture was heated at 100° C. for 4 hours. After completion of the reaction, water was added to the reactant at 0° C., and then the reactant was stirred for 2 hours. The reactant was filtered to obtain a solid, and then the solid was washed with water and dried to give the title compound (6.0 g, Yield 49%).
¹H-NMR (400 HMz, CDCl₃); δ 10.32 (br s, 1H), 8.29 (d, 1H), 8.03 (d, J=2.4 Hz, 1H), 7.31 (d, J=2.0 Hz, 1H), 4.01 (s, 3H)

Step D: 5-Chloro-7-nitro-1H-indol-2-carboxylic acid

5-Chloro-7-nitro-1H-indol-2-carboxylic acid methyl ester (1.0 g, 3.93 mmol) obtained in Step C was dissolved in the mixture solution of THF (10 ml), MeOH (10 mL) and water (10 mL). And then lithium hydroxide (330 mg, 7.87 mmol) was added thereto, and the mixture was stirred at room temperature for 18 hours. After completion of the reaction, 0.5 N HCl (20 ml) and water (100 ml) was added thereto for crystallization. The reactant was then filtered to give the title compound (870 mg, Yield 92%).
MS[M+1]=241 (M+1)

PREPARATION EXAMPLE 2

5-Methyl-7-nitro-1H-indol-2-carboxylic acid

Commercially available 4-methyl-2-nitro-aniline was reacted in the same manner as in Preparation Example 1 to give the title compound.
MS[M+1]=221 (M+1)

PREPARATION EXAMPLE 3

5-Bromo-7-nitro-1H-indol-2-carboxylic acid

Commercially available 4-bromo-2-nitro-aniline was reacted in the same manner as in Preparation Example 1 to give the title compound.
MS[M+1]=286 (M+1)

EXAMPLE 1

5-Chloro-7-cyclopentylamino-1H-indol-2-carboxylic acid (4-phenoxy-phenyl)-amide

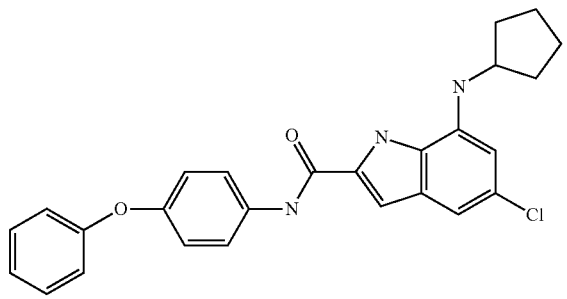

5-Chloro-7-cyclopentylamino-1H-indole-2-carboxylic acid (4-phenoxy-phenyl)-amide

Step A: 5-Chloro-7-nitro-1H-indol-2-carboxylic acid (4-phenoxy-phenyl)-amide 5-Chloro-7-nitro-1H-indol-2-carboxylic acid (1.0 g, 4.16 mmol) obtained in Preparation Example 1 was dissolved in DMF (30 mL), and then trimethylamine (841 mg, 8.31 mmol), HBTU (2.36 g, 6.22 mmol) and 4-phenoxyphenylamine (0.92 g, 5.05 mmol) were added thereto. The mixture was stirred at room temperature for 18 hours. After completion of the reaction, the solvent was removed under reduced pressure, and sodium bicarbonate solution (100 ml) was added thereto. Organic material was extracted with ethyl acetate, and dried with anhydrous magnesium sulfate. The solvent was removed from the filtrate under reduced pressure, and the residue was purified by column chromatography to give the title compound (1.6 g, Yield 94%).
MS[M+1]=408 (M+1)

Step B: 7-Amino-5-chloro-1H-indol-2-carboxylic acid (4-phenoxy-phenyl)-amide 5-Chloro-7-nitro-1H-indol-2-carboxylic acid (4-phenoxy-phenyl)-amide (1.6 g, 2.92 mmol) obtained in Step A was dissolved in THF (15 mL), methanol (15 mL) and water (15 mL), and then ammonium chloride (2.62 g, 49.0 mmol) and iron powder (1.34 g, 24.0 mmol) were added thereto. The mixture was stirred at 70° C. for 1 hour. After completion of the reaction, the reactant was filtered through Cellite and washed with tetrahydrofuran (100 mL), and the solvent was removed under reduced pressure. The reactant was diluted with ethyl acetate (150 mL), and water (80 mL) was added thereto. Organic material was extracted with ethyl acetate and dried with anhydrous magnesium sulfate, and the solvent was removed under reduced pressure. The residue was recrystallized with dichloromethane and hexane to give the title compound (1.4 g, Yield 94%).
MS[M+1]=378 (M+1)

Step C: 5-Chloro-7-cyclopentylamino-1H-indol-2-carboxylic acid (4-phenoxy-phenyl)-amide 7-Amino-5-chloro-1H-indol-2-carboxylic acid (4-phenoxy-phenyl)-amide (50 mg, 0.13 mmol) obtained in Step B was dissolved in dichloroethane (10 mL), and then acetic acid (16 mg, 0.27 mmol), cyclopentanone (0.30 mg, 0.40 mmol) and sodium triacetoxy borohydride (84 mg, 0.40 mmol) were added dropwise thereto. The mixture was stirred at room temperature for 18 hours. After completion of the reaction, the reactant was diluted with water. Organic material was extracted with dichloromethane, washed with saturated sodium chloride solution, dried with anhydrous magnesium sulfate, and filtered. The solvent was removed under reduced pressure, and the residue was purified by column chromatography to give the title compound (40 mg, Yield 68%).
MS[M+1]=446 (M+1)

EXAMPLE 2

5-Chloro-7-(pyrrolidin-3-ylamino)-1H-indol-2-carboxylic acid (4-phenoxy-phenyl)-amide

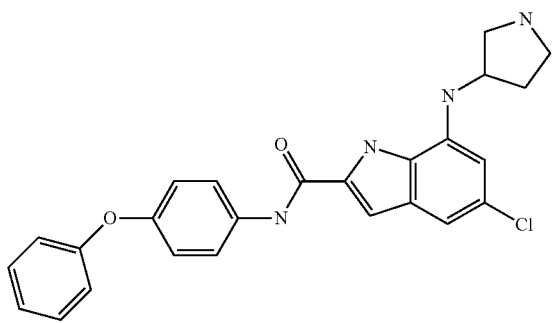

5-Chloro-7-(pyrrolidin-3-ylamino)-1H-indole-2-carboxylic acid (4-phenoxy-phenyl)-amide Step A: 3-[5-Chloro-2-(4-phenoxy-phenylcarbamoyl)-1H-indol-7-ylamino]-pyrrolidin-1-carboxylic acid t-butyl ester 7-Amino-5-chloro-1H-indol-2-carboxylic acid (4-phenoxy-phenyl)-amide obtained in Step B of Example 1 and N-BOC-pyrrolidin-3-one were reacted in the same manner as in Step C of Example 1 to give the title compound.
MS[M+1]=547 (M+1)

Step B: 5-Chloro-7-(pyrrolidin-3-ylamino)-1H-indol-2-carboxylic acid (4-phenoxy-phenyl)-amide 3-[5-chloro-2-(4-phenoxy-phenylcarbamoyl)-1H-indol-7-ylamino]-pyrrolidin-1-carboxylic acid t-butyl ester (45 mg, 0.082 mmol) obtained in Step A was dissolved in dichloromethane (3 ml), and then trifluoroacetic acid (3 ml) was added thereto. The mixture was stirred at room temperature for 1 hour. After completion of the reaction, the solvent was removed under reduced pressure. The residue was purified by column chromatography to give the title compound (18 mg, Yield 49%).
MS[M+1]=447 (M+1)

EXAMPLES 3-35

Indole compounds obtained in Preparation Examples 1 to 3 and commercially available amine compounds were reacted in the same manner as in Example 1 or 2 to give the compounds in the following table.

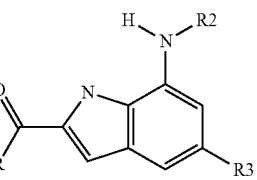

| Example | R | R2 | R3 | Mass |
|---|---|---|---|---|
| 3 | 4-(3,4-difluorophenyloxy)phenyl-amino | piperidin-4-yl | Cl | 497 |
| 4 | 3-phenoxy-phenyl-amino | piperidin-4-yl | Cl | 461 |
| 5 | benzylamino | pyrrolidin-2-ylmethyl | Cl | 383 |
| 6 | 4-phenoxy-phenyl-amino | piperidin-3-yl | Cl | 461 |
| 7 | 4-phenoxy-phenyl-amino | piperidin-4-yl | Cl | 461 |
| 8 | 3-phenoxy-phenyl-amino | pyrrolidin-2-ylmethyl | Cl | 461 |
| 9 | 3-cyclopentyloxy-5-phenoxy-phenyl-amino | pyrrolidin-2-ylmethyl | Cl | 545 |
| 10 | 4-phenoxy-phenyl-amino | pyrrolidin-2-ylmethyl | Cl | 461 |
| 11 | 4-(3,4-difluorophenyloxy)phenyl-amino | 2-amino-pyridin-3-ylmethyl | Cl | 520 |
| 12 | 3-cyclopentyloxy-phenylamino | piperidin-4-yl | Cl | 453 |
| 13 | 3-(morpholin-4-yl)methyl-phenylamino | piperidin-4-yl | Cl | 468 |
| 14 | 3-phenyl-phenylamino | piperidin-4-yl | Cl | 445 |
| 15 | 3-benzyloxy-phenyl-amino | piperidin-4-yl | Cl | 475 |
| 16 | 4-trifluoromethyloxy-phenylamino | piperidin-4-yl | Cl | 453 |
| 17 | 4-(3,5-dimethyl-phenyloxy)-phenylamino | piperidin-4-yl | Cl | 489 |
| 18 | 3-fluorophenyl-ethylamino | piperidin-4-yl | Cl | 415 |
| 19 | 3-phenoxy-phenylamino | thiazol-2-ylmethyl | Cl | 474 |
| 20 | 4-isopentyloxy-phenylamino | piperidin-4-yl | Cl | 455 |
| 21 | 4-(3,4-dimethyl-phenyloxy)-phenylamino | pyrrolidin-2-ylmethyl | Cl | 489 |
| 22 | pyrrolidin-1-yl | cyclopentyl | Cl | 332 |
| 23 | (R)-3-methoxycarbonyl-pyrrolidin-1-yl | cyclopentyl | Cl | 390 |
| 24 | (R)-3-methoxycarbonyl-pyrrolidin-1-yl | cyclopentyl-methyl | Cl | 404 |
| 25 | (R)-3-methoxycarbonyl-pyrrolidin-1-yl | tetrahydro-pyran-4-yl | Cl | 406 |
| 26 | (S)-3-methoxycarbonyl-pyrrolidin-1-yl | tetrahydro-pyran-4-yl | Me | 386 |
| 27 | morpholine | cyclohexyl | Br | 406 |
| 28 | morpholine | cyclopentyl | Me | 328 |
| 29 | piperazine | cyclopentyl | Me | 327 |
| 30 | 1-benzyl-pyrrolidin-3-ylmethylamino | cyclopentyl | Cl | 451 |
| 31 | 2-dimethylamino-ethylamino | cyclopentyl | Me | 329 |
| 32 | 2-morpholin-4-yl-ethylamino | cyclopentyl | Me | 371 |
| 33 | 4-benzyl-piperazin-1-yl | piperidin-4-yl | Cl | 452 |
| 34 | (R)-3-(3,4-difluoro-phenoxy-methyl)pyrrolidin-1-yl | piperidin-4-yl | Cl | 489 |
| 35 | (R)-3-(phenoxy methyl)pyrrolidin-1-yl | piperidin-4-yl | Cl | 453 |

EXAMPLE 36

(R)-1-[5-chloro-7-(tetrahydro-pyran-4-ylamino)-1H-indol-2-carbonyl]-pyrrolidin-3-carboxylic acid

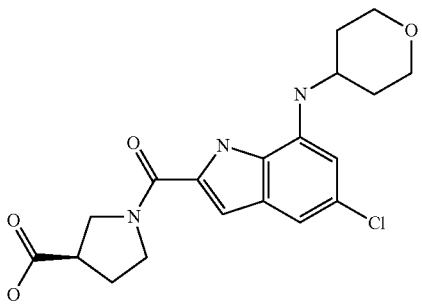

(R)-1-[5-Chloro-7-(tetrahydro-pyran-4-ylamino)-1H-indole-2-carbonyl]-pyrrolidine-3-carboxylic acid (R)-1-[5-chloro-7-(tetrahydro-pyran-4-ylamino)-1H-indol-2-carbonyl]-pyrrolidin-3-carboxylic acid methyl ester obtained in Example 25 was reacted in the same manner as in Step D of Preparation Example 1 to give the title compound.
MS[M+I]=392 (M+1)

EXAMPLE 37

[5-Chloro-7-(tetrahydropyran-4-ylamino)-1H-indol-2-yl]-((R)-3-hydroxymethyl-pyrrolidin-1-yl)-methanone

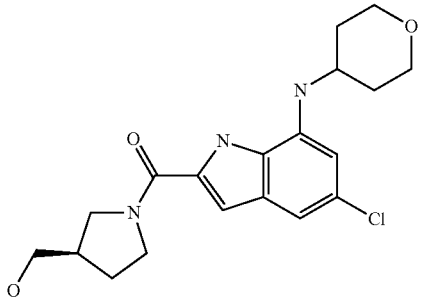

[5-Chloro-7-(tetrahydro-pyran-4-ylamino)-1H-indol-2-yl]-((R)-3-hydroxymethyl-pyrrolidin-1-yl)-methanone (R)-1-[5-chloro-7-(tetrahydropyran-4-ylamino)-1H-indol-2-carbonyl]-pyrrolidin-3-carboxylic acid methyl ester (44 mg, 0.11 mmol) obtained in Example 25 was dissolved in THF (15 ml), and then 2.0 M lithium borohydride (0.11 ml) was added thereto at 0° C. The mixture was stirred for 6 hours. After completion of the reaction, methanol (2 ml) and 1N-hydrochloric acid solution (20 ml) were slowly added thereto. Organic material was extracted with ethyl acetate and dried with anhydrous magnesium sulfate. After filtering, the solvent was removed from the filtrate under reduced pressure, and the residue was purified by column chromatography to give the title compound (30 mg, Yield 73%).
MS[M+1]=378 (M+1)

EXAMPLE 38

(S)-1-[5-methyl-7-(tetrahydropyran-4-ylamino)-1H-indol-2-carbonyl]-pyrrolidin-3-carboxylic acid

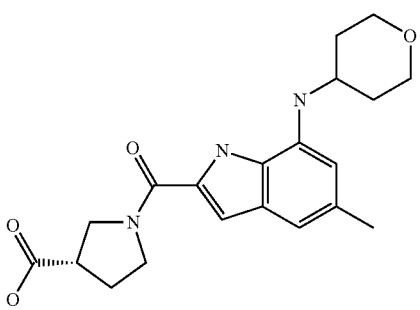

(S)-1-[5-Methyl-7-(tetrahydro-pyran-4-ylamino)-1H-indole-2-carbonyl]-pyrrolidine-3-carboxylic acid (S)-1-[5-methyl-7-(tetrahydro-pyran-4-ylamino)-1H-indol-2-carbonyl]-pyrrolidin-3-carboxylic acid methyl ester obtained in Example 26 was reacted in the same manner as in Example 36 to give the title compound.
MS[M+1]=372 (M+1)

EXAMPLE 39

7-(2-Amino-acetylamino)-5-chloro-1H-indol-2-carboxylic acid (4-phenoxy-phenyl)-amide

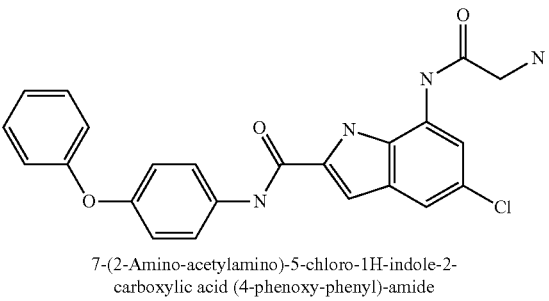 [SMILES: NCC(=O)Nc1cc(Cl)cc2cc(C(=O)Nc3ccc(Oc4ccccc4)cc3)[nH]c12]

7-(2-Amino-acetylamino)-5-chloro-1H-indole-2-carboxylic acid (4-phenoxy-phenyl)-amide Step A: {[5-Chloro-2-(4-phenoxy-phenylcarbamoyl)-1H-indol-7-ylcarbamoyl]-methyl}-carbamic acid t-butyl ester The compound obtained in Step B of Example 1 and N-BOC-glycine were reacted in the same manner as in Step A of Example 1 to give the title compound.
MS[M+1]=535 (M+1)

Step B: 7-(2-Amino-acetylamino)-5-chloro-1H-indol-2-carboxylic acid (4-phenoxy-phenyl)-amide {[5-Chloro-2-(4-phenoxy-phenylcarbamoyl)-1H-indol-7-ylcarbamoyl]-methyl}-carbamic acid t-butyl ester obtained in Step A was reacted in the same manner as in Step B of Example 2 to give the title compound.
MS[M+1]=435 (M+1)

EXAMPLE 40

(3-Aminomethyl-pyrrolidin-1-yl)-(5-chloro-7-cyclopentylamino-1H-indol-2-yl)-methanone

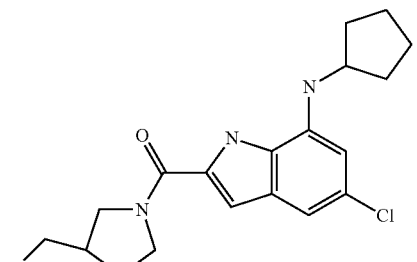

(3-Aminomethyl-pyrrolidin-1-yl)-(5-chloro-7-cyclopentylamino-1H-indol-2-yl)-methanone Step A: [1-(5-chloro-7-cyclopentylamino-1H-indol-2-carbonyl)-pyrrolidin-3-ylmethyl]-carbamic acid t-butyl ester 5-Chloro-7-nitro-1H-indol-2-carboxylic acid obtained in Preparation Example 1 and pyrrolidin-3-ylmethyl-carbamic acid t-butyl ester were reacted in the same manner as in Example 1 to give the title compound.
MS[M+I]=461 (M+1)

Step B: (3-Aminomethyl-pyrrolidin-1-yl)-(5-chloro-7-cyclopentylamino-1H-indol-2-yl)-methanone

[1-(5-Chloro-7-cyclopentylamino-1H-indol-2-carbonyl)-pyrrolidin-3-ylmethyl]-carbamic acid t-butyl ester obtained in Step A was reacted in the same manner as in Step B of Example 2 to give the title compound.
MS[M+1]=361 (M+1)

EXAMPLE 41

(5-chloro-7-cyclopentylamino-1H-indol-2-yl)-(3-piperidin-1-ylmethyl-pyrrolidin-1-yl)-methanone

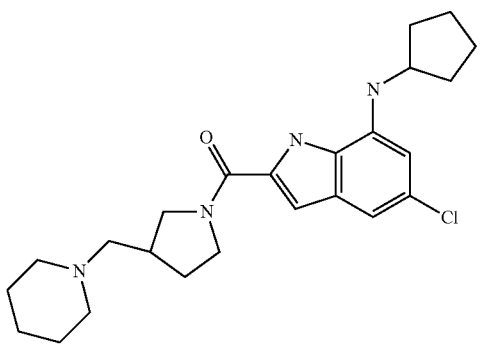

(5-Chloro-7-cyclopentylamino-1H-indol-2-yl)-(3-piperidin-1-ylmethyl-pyrrolidin-1-yl)-methanone (3-Aminomethyl-pyrrolidin-1-yl)-(5-chloro-7-cyclopentylamino-1H-indol-2-yl)-methanone obtained in Example 40 and glutaraldehyde were reacted in the same manner as in Step C of Example 1 to give the title compound.
MS[M+1]=429 (M+1)

EXAMPLES 42-57

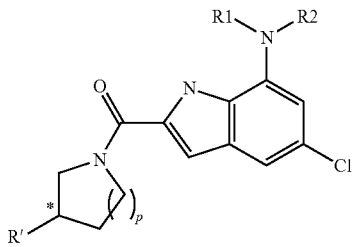

| Example | R' | p | * | R1 | R2 | Mass |
|---|---|---|---|---|---|---|
| 42 | piperidin-1-ylmethyl | 1 | — | H | tetrahydropyran-4-yl | 445 |
| 43 | aminomethyl | 1 | — | H | tetrahydropyran-4-yl | 377 |
| 44 | amino | 1 | R | H | cyclopentyl | 347 |
| 45 | 3-dimethylaminobenzyl aminomethyl | 1 | — | H | cyclopentyl | 494 |
| 46 | aminomethyl | 1 | — | H | isopentyl | 363 |
| 47 | aminomethyl | 1 | — | H | cyclopentylmethyl | 375 |
| 48 | aminomethyl | 1 | — | —(CH$_2$)$_5$— | | 361 |
| 49 | aminomethyl | 1 | — | H | penethyl | 383 |
| 50 | aminomethyl | 1 | — | H | n-pentyl | 363 |
| 51 | aminomethyl | 1 | — | H | cyclohexyl | 375 |
| 52 | aminomethyl | 2 | — | H | cyclopentyl | 375 |
| 53 | aminomethyl | 1 | — | cyclopropylmethyl | cyclopropylmethyl | 401 |
| 54 | aminomethyl | 1 | — | isopentyl | isopentyl | 433 |
| 55 | amino | 1 | S | H | cyclopentyl | 347 |
| 56 | 4-fluoro benzylaminomethyl | 1 | — | isopentyl | isopentyl | 541 |
| 57 | 3,4-difluoro benzylaminomethyl | 1 | — | isopentyl | isopentyl | 559 |

EXAMPLE 58

(3-Aminomethyl-pyrrolidin-1-yl)-(5-bromo-7-cyclopentylamino-1H-indol-2-yl)-methanone

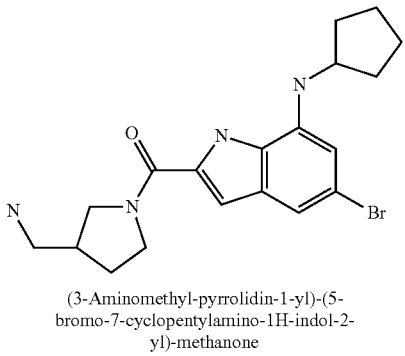 [SMILES: NCC1CCN(C(=O)c2cc3cc(Br)cc(NC4CCCC4)c3[nH]2)C1]

(3-Aminomethyl-pyrrolidin-1-yl)-(5-bromo-7-cyclopentylamino-1H-indol-2-yl)-methanone 5-Bromo-7-nitro-1H-indol-2-carboxylic acid obtained in Preparation Example 3 was reacted in the same manner as in Example 40 to give the title compound.
MS[M+1]=406 (M+1)

EXAMPLE 59

7-Cyclopentylamino-5-methyl-1H-indol-2-carboxylic acid (pyrrolidin-3-ylmethyl)-amide

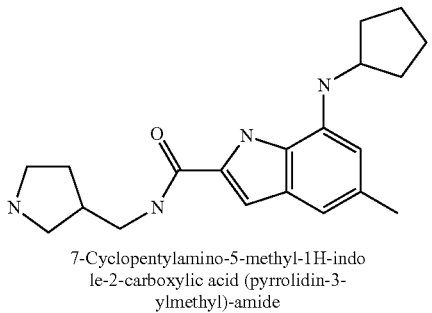 [SMILES: Cc1cc(NC2CCCC2)c2[nH]c(C(=O)NCC3CCNC3)cc2c1]

7-Cyclopentylamino-5-methyl-1H-indole-2-carboxylic acid (pyrrolidin-3-ylmethyl)-amide 5-Methyl-7-nitro-1H-indol-2-carboxylic acid obtained in Preparation Example 2 and 3-aminomethyl-pyrrolidin-1-carbamic acid t-butyl ester were reacted in the same manner as in Example 40 to give the title compound.
MS[M+1]=341 (M+1)

PREPARATION EXAMPLE 4

(3R,4S)-3-(2,4-difluoro-phenyl)-4-pyrrolidin-1-ylmethyl-pyrrolidin

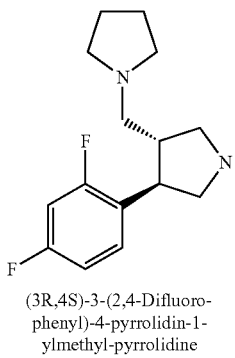 [SMILES: Fc1ccc([C@@H]2CNC[C@H]2CN2CCCC2)c(F)c1]

(3R,4S)-3-(2,4-Difluorophenyl)-4-pyrrolidin-1-ylmethyl-pyrrolidine

Step A: (4R)-4-(2,4-difluorophenyl)pyrrolidin-3-carbonitrile (4R)-1-t-butyl-4-(2,4-difluorophenyl)pyrrolidin-3-carbonitrile (4 g, 15.15 mmol) prepared by a method disclosed in International Publication No. WO 2004/09126 was dissolved in DCE (10 mL), and 1-chloroethyl chloroformate (2.45 ml, 22.68 mmol) was then added dropwise thereto at 0° C. After heating to 70° C., 1,8-bis(dimethylamino)naphthalene (4.87 g, 22.72 mmol) dissolved in DCE (10 mL) was added dropwise thereto for 2 hours, while maintaining the temperature. After completion of the reaction, MeOH (10 mL) was added thereto. The mixture was further stirred for 1 hour while maintaining the temperature. The reactant was then concentrated under vacuum, and the next reaction was performed without purification.
MS[M+1]=209 (M+1)

Step B: (4R)-1-BOC-4-(2,4-difluorophenyl)pyrrolidin-3-carbonitrile (4R)-4-(2,4-difluorophenyl)pyrrolidin-3-carbonitrile obtained in Step A, DMAP (1.8 g, 15.15 mmol) and TEA (5.56 mL, 15.15 mmol) were dissolved in DCM (10 mL), and di-t-butyl dicarbonate (4.9 g, 22.7 mmol) was then added dropwise at 0° C. The reactant was stirred at room temperature for 8 hours, concentrated under vacuum, and extracted with EtOAc. Extracted organic solution was washed with 1 N HCl and saline solution, dried with MgSO$_4$, concentrated under vacuum, and purified by column chromatography (eluent: EtOAc/Hex=⅙) to give the title compound (3.3 g, sum of Steps A and B: 72%).
MS[M+H]=309 (M+1)

Step C: (3S,4R)-1-BOC-4-(2,4-difluorophenyl)pyrrolidin-3-carboxylic acid (4R)-1-BOC-4-(2,4-difluorophenyl)pyrrolidin-3-carbonitrile (3.3 g, 10.6 mmol) obtained in Step B was dissolved in ethanol (10 mL), then 6 N NaOH solution (5 mL) was added thereto, and the mixture was stirred at 70° C. for 4 hours. After completion of the reaction, the solvent was removed and the reactant was diluted with ether. The organic solution was fully acidified and washed with 6N hydrochloric acid. After the organic solution was washed with saline solution, the reactant was dried with MgSO$_4$ and concentrated under vacuum to give the title compound (3.43 g, 99.0%).
MS[M+1]=328 (M+1)

Step D: (3S,4R)-1-BOC-4-(2,4-difluorophenyl)pyrrolidin-3-methylalcohol (3S,4R)-1-BOC-4-(2,4-difluorophenyl)pyrrolidin-3-carboxylic acid (400 mg, 1.22 mmol) obtained in Step C was dissolved in THF (15 ml), and N-methylmorpholine (140 mg, 1.35 mmol) and isobutylchloroformate (183 mg, 1.34 mmol) were then added thereto at −15° C. The mixture was stirred for 15 minutes. After completion of the reaction, sodium borohydride (59.5 mg, 1.57 mmol) was added thereto, and methanol (5 ml) was slowly added thereto, and then the mixture was stirred for 1 hour. After completion of the reaction, 1N-hydrochloric acid solution was added thereto. Organic material was extracted with ethyl acetate and dried with anhydrous magnesium sulfate. After filtering, the solvent was removed from the filtrate under reduced pressure, and the residue was purified by column chromatography to give the title compound (300 mg, Yield 79%).
MS[M+1]=314 (M+1)

Step E: (3S,4R)-1-BOC-4-(2,4-difluorophenyl)pyrrolidin-3-carboxaldehyde (3S,4R)-1-BOC-4-(2,4-difluorophenyl)pyrrolidin-3-methyl alcohol (296 mg, 0.95 mmol) obtained in Step D was dissolved in dichloromethane (40 ml) and methylsulfoxide (10 ml), and trimethylamine (337 mg, 3.33 mmol) and sulfurtrioxide pyridine (230 mg, 1.42 mmol) were then added thereto. The mixture was stirred at room temperature for 2 hours. After completion of the reaction, water was added thereto, and the organic material was extracted with ethyl acetate, washed with saturated aqueous sodium chloride, dried with anhydrous magnesium sulfate, and filtered. The solvent was removed under reduced pressure, and the residue was purified by column chromatography to give the title compound (246 mg, Yield 83%).
MS[M+1]=312 (M+1)

Step F: (3R,4S)-3-(2,4-difluoro-phenyl)-4-pyrrolidin-1-ylmethyl-pyrrolidin (3S,4R)-1-BOC-4-(2,4-difluorophenyl)pyrrolidin-3-carboxaldehyde obtained in Step E and pyrrolidine were reacted in the same manner as in Step C of Example 1 and Step B of Example 2 sequentially to give the title compound.
MS[M+1]=267 (M+1)

PREPARATION EXAMPLE 5

(3R,4S)-3-(4-chloro-phenyl)4-pyrrolidin-1-ylmethyl-pyrrolidin 3-(4-chlorophenyl)pyrrolidin-4-carbonitrile was reacted in the same manner as in Preparation Example 4 to give the title compound.
MS[M+1]=265 (M+1)

EXAMPLE 60

{7-[Bis-(3-methyl-butyl)-amino]-5-chloro-1H-indol-2-yl}-[(3R,4R)-3-(2,4-difluoro-phenyl)-4-pyrrolidin-1-ylmethyl-pyrrolidin-1-yl]-methanone

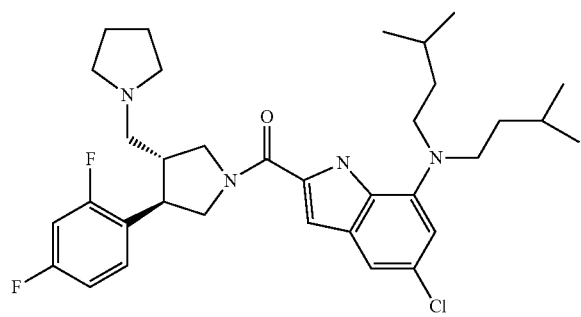

{7-[Bis-(3-methyl-butyl)-amino]-5-chloro-1H-indol-2-yl}-[(3R,4R)-3-(2,4-difluoro-phenyl)-4-pyrrolidin-1-ylmethyl-pyrrolidin-1-yl]-methanone 5-Chloro-7-nitro-1H-indol-2-carboxylic acid obtained in Preparation Example 1, (3R,4S)-3-(2,4-difluoro-phenyl)-4-pyrrolidin-1-ylmethyl-pyrrolidin obtained in Preparation Example 4 and isobutyl aldehyde were reacted in the same manner as in Example 1 to give the title compound.
MS[M+1]=599 (M+1)

EXAMPLE 61

{7-[Bis-(3-methyl-butyl)-amino]-5-chloro-1H-indol-2-yl}-[(3R,4R)-3-(4-chloro-phenyl)-4-pyrrolidin-1-ylmethyl-pyrrolidin-1-yl]-methanone

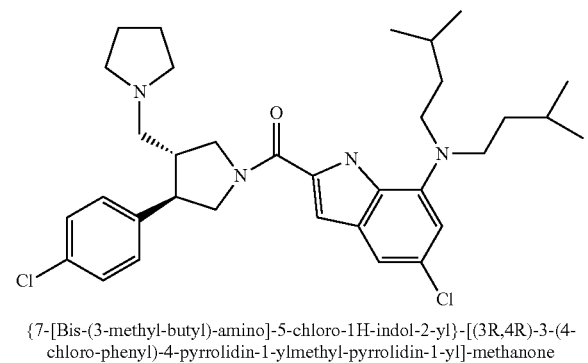 [SMILES: CC(C)CCN(CCC(C)C)c1cc(Cl)cc2cc(C(=O)N3C[C@@H](CN4CCCC4)[C@H](c4ccc(Cl)cc4)C3)[nH]c12]

{7-[Bis-(3-methyl-butyl)-amino]-5-chloro-1H-indol-2-yl}-[(3R,4R)-3-(4-chloro-phenyl)-4-pyrrolidin-1-ylmethyl-pyrrolidin-1-yl]-methanone 5-chloro-7-nitro-1H-indol-2-carboxylic acid obtained in Preparation Example 1, (3R,4S)-3-(4-chloro-phenyl)-4-pyrrolidin-1-ylmethyl-pyrrolidin obtained in Preparation Example 5 and isobutyl aldehyde were reacted in the same manner as in Example 1 to give the title compound.
MS[M+1]=597 (M+1)

EXAMPLE 62

(5-Chloro-7-cyclopentylamino-1H-indol-2-yl}-[(3R,4R)-3-(2,4-difluoro-phenyl)-4-pyrrolidin-1-ylmethyl-pyrrolidin-1-yl]-methanone

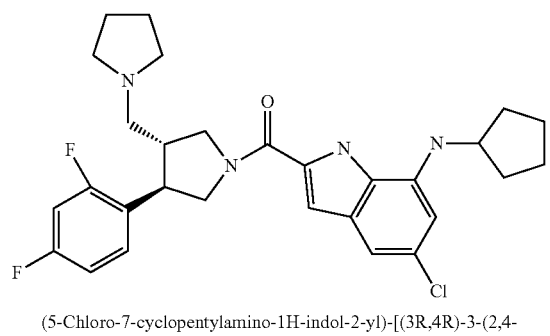

(5-Chloro-7-cyclopentylamino-1H-indol-2-yl)-[(3R,4R)-3-(2,4-difluoro-phenyl)-4-pyrrolidin-1-ylmethyl-pyrrolidin-1-yl]-methanone 5-Chloro-7-nitro-1H-indol-2-carboxylic acid obtained in Preparation Example 1, (3R,4S)-3-(2,4-difluoro-phenyl)-4-pyrrolidin-1-ylmethyl-pyrrolidine obtained in Preparation Example 4 and cyclopentanone were reacted in the same manner as in Example 1 to give the title compound.
MS[M+1]=527 (M+1)

EXAMPLE 63

(5-Chloro-7-(tetrahydropyran-4-ylamino)-1H-indol-2-yl}-[(3R,4R)-3-(2,4-difluoro-phenyl)-4-pyrrolidin-1-ylmethyl-pyrrolidin-1-yl]-methanone

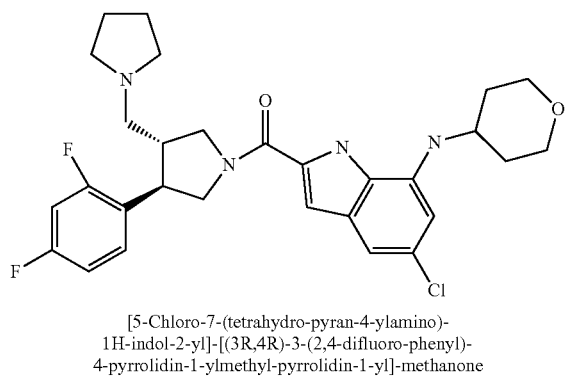 [SMILES: O=C(c1cc2cc(Cl)cc(NC3CCOCC3)c2[nH]1)N1C[C@@H](CN2CCCC2)[C@H](c2ccc(F)cc2F)C1]

[5-Chloro-7-(tetrahydro-pyran-4-ylamino)-1H-indol-2-yl]-[(3R,4R)-3-(2,4-difluoro-phenyl)-4-pyrrolidin-1-ylmethyl-pyrrolidin-1-yl]-methanone 5-Chloro-7-nitro-1H-indol-2-carboxylic acid obtained in Preparation Example 1, (3R,4S)-3-(2,4-difluoro-phenyl)-4-pyrrolidin-1-ylmethyl-pyrrolidine obtained in Preparation Example 4 and tetrahydropyran-4-one were reacted in the same manner as in Example 1 to give the title compound.
MS[M+1]=543 (M+1)

EXAMPLE 64

(5-Chloro-7-(piperidin-4-ylamino)-1H-indol-2-yl}-[(3R,4R)-3-(2,4-difluoro-phenyl)-4-pyrrolidin-1-ylmethyl-pyrrolidin-1-yl]-methanone

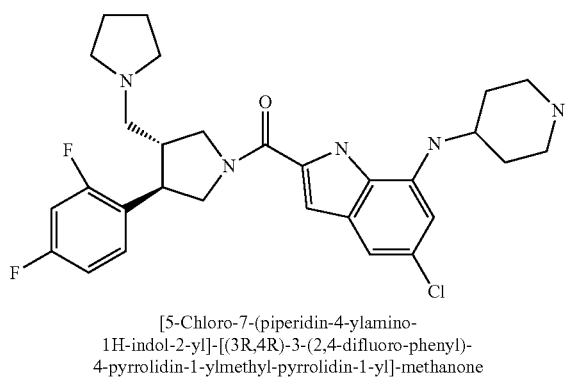 [SMILES: O=C(c1cc2cc(Cl)cc(NC3CCNCC3)c2[nH]1)N1C[C@@H](CN2CCCC2)[C@H](c2ccc(F)cc2F)C1]

[5-Chloro-7-(piperidin-4-ylamino-1H-indol-2-yl]-[(3R,4R)-3-(2,4-difluoro-phenyl)-4-pyrrolidin-1-ylmethyl-pyrrolidin-1-yl]-methanone 5-Chloro-7-nitro-1H-indol-2-carboxylic acid obtained in Preparation Example 1, (3R,4S)-3-(2,4-difluoro-phenyl)-4-pyrrolidin-1-ylmethyl-pyrrolidine obtained in Preparation Example 4 and 1-BOC-piperidin-4-one were reacted in the same manner as in Example 1 and Step B of Example 2 to give the title compound.
MS[M+1]=542 (M+1)

PREPARATION EXAMPLE 6

((R)-2-phenyl-1-pyrrolidin-1-ylmethyl-ethylamine

Commercially available ((R)-1-hydroxymethyl-2-phenyl-ethyl)-carbamic acid t-butyl ester was reacted in the same manner as in Steps E and F of Preparation Example 4 sequentially to give the title compound.
MS[M+1]=205 (M+1)

EXAMPLE 65

(5-Chloro-7-cyclopentylamino)-1H-indol-2-carboxylic acid ((R)-2-phenyl-1-pyrrolidin-1-ylmethyl-ethyl)-amide

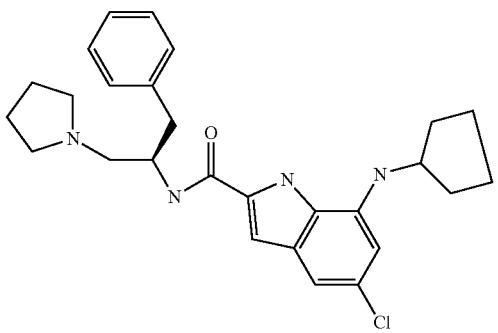

5-Chloro-7-cyclopentylamino-1H-indole-2-carboxylic acid ((R)-2-phenyl-1-pyrrolidin-1-ylmethyl-ethyl)-amide 5-Chloro-7-nitro-1H-indol-2-carboxylic acid obtained in Preparation Example 1, ((R)-2-phenyl-1-pyrrolidin-1-ylmethyl)-ethylamine obtained in Preparation Example 6 and cyclopentanone were reacted in the same manner as in Example 1 to give the title compound.
MS[M+1]=465 (M+1)

EXAMPLE 66

[5-Methyl-2-(pyrrolidin-1-carbonyl)-1H-indol-7-ylamino]-acetic acid

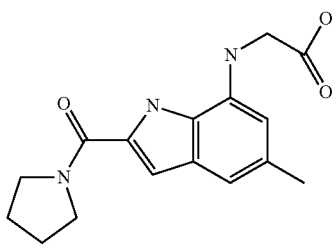

[5-Methyl-2-(pyrrolidine-1-carbonyl)-1H-indol-7-ylamino]-acetic acid

Step A: (7-Amino-5-methyl-1H-indol-2-yl)-pyrrolidin-1-yl-methanone

5-Methyl-7-nitro-1H-indol-2-carboxylic acid obtained in Preparation Example 2 and pyrrolidine were reacted in the same manner as in Steps A and B of Example 1 sequentially to give the title compound.
MS[M+1]=244 (M+1)

Step B: 5-Methyl-2-(pyrrolidin-1-carbonyl)-1H-indol-7-ylamino]-acetic acid methyl ester (7-Amino-5-methyl-1H-indol-2-yl)-pyrrolidin-1-yl-methanone (100 mg, 0.41 mmol) obtained in Step A was dissolved in THF, and trimethylamine (46 mg, 0.45 mmol) and bromoacetic acid methyl ester (70 mg, 0.45 mmol) were then added thereto. The mixture was stirred at 80° C. for 4 hours. After completion of the reaction, water was added thereto. The organic material was extracted with ethyl acetate, washed with aqueous saturated sodium chloride, dried with anhydrous magnesium sulfate, and filtered. The solvent was removed under reduced pressure, and the residue was purified by column chromatography to give the title compound (80 mg, Yield 62%).

MS[M+1]=316 (M+1)

Step C: [5-Methyl-2-(pyrrolidin-1-carbonyl)-1H-indol-7-ylamino]-acetic acid

5-Methyl-2-(pyrrolidin-1-carbonyl)-1H-indol-7-ylamino]-acetic acid methyl ester obtained in Step B was reacted in the same manner as in Step D of Preparation Example 1 to give the title compound

MS[M+1]=302 (M+1)

PREPARATION EXAMPLE 7

5-Bromomethyl-7-nitro-indol-2-carboxylic acid methyl ester

Step A: 1-BOC-5-methyl-7-nitro-indol-2-carboxylic acid methyl ester

5-Methyl-7-nitro-1H-indol-2-carboxylic acid methyl ester (24.0 g, 100 mmol) which is formed during the synthesis of the compound of Preparation Example 2 was dissolved in dichloromethane (500 mL), and trimethylamine (84 mL, 601 mmol) and 4-(dimethylamino)pyridine (600 mg, 5 mmol) were then added thereto. (BOC)$_2$O (43.7 g, 200 mmol) dissolved in dichloromethane (100 mL) was added dropwise thereto, and the mixture was stirred at room temperature for 8 hours. After completion of the reaction, water was added thereto. The organic material was extracted with ethyl acetate, washed with aqueous saturated sodium chloride, dried with anhydrous magnesium sulfate and concentrated under vacuum to give the title compound (34.0 g, Yield 100%).

$^1$H-NMR (500 HMz, CDCl$_3$); δ 7.80 (s, 1H), 7.67 (s, 1H), 7.15 (s, 1H), 3.93 (s, 3H), 2.51 (s, 3H), 1.62 (s, 9H)

Step B: 1-BOC-5-bromomethyl-7-nitro-indol-2-carboxylic acid methyl ester

1-BOC-5-methyl-7-nitro-indol-2-carboxylic acid methyl ester (34 g, 101.7 mmol) obtained in Step A was dissolved in carbon tetrachloride (100 mL), and N-bromosuccinimide (27.2 g, 152.6 mmol) and AIBN (1.7 g, 10.2 mmol) were then added thereto. The mixture was stirred at 80° C. for 5 hours. After completion of the reaction, the reactant was distilled under vacuum, and purified by column chromatography to give the title compound (48.0 g, Yield 100%).

$^1$H-NMR (500 HMz, CDCl$_3$); δ 8.01 (s, 1H), 7.90 (s, 1H), 7.21 (s, 1H), 4.60 (s, 2H), 3.93 (s, 3H), 1.62 (s, 9H)

Step C: 5-bromomethyl-7-nitro-indol-2-carboxylic acid methyl ester

1-BOC-5-bromomethyl-7-nitro-indol-2-carboxylic acid methyl ester obtained in Step B was reacted in the same manner as in Step B of Example 2 to give the title compound.

Mass [M+H]=314 (M+1)

PREPARATION EXAMPLE 8

5-(1,1-Dioxo-thiomorpholin-4-ylmethyl)-7-nitro-1H-indol-2-carboxylic acid

Step A: 5-(1,1-Dioxo-thiomorpholin-4-ylmethyl)-7-nitro-1H-indol-2-carboxylic acid methyl ester 5-Bromomethyl-7-nitro-indol-2-carboxylic acid methyl ester (2.4 g, 7.67 mmol) obtained in Preparation Example 7 was dissolved in acetonitrile, and thiomorpholine 1,1-dioxide (1.04 mg, 15.3 mmol) was then added thereto. The mixture was stirred at 80° C. for 6 hours. After completion of the reaction, the solvent was removed under reduced pressure, and water (100 ml) was added thereto. The organic material was extracted with ethyl acetate and dried with anhydrous magnesium sulfate. The solvent was removed under reduced pressure, and the residue was purified by column chromatography to give the title compound (2.1 g, Yield 75%).

MS[M+1]=368 (M+1)

Step B: 5-(1,1-Dioxo-thiomorpholin-4-ylmethyl)-7-nitro-1H-indol-2-carboxylic acid 5-(1,1-Dioxo-thiomorpholin-4-ylmethyl)-7-nitro-1H-indol-2-carboxylic acid methyl ester obtained in Step A was reacted in the same manner as in Step D of Preparation Example 1 to give the title compound.

MS[M+1]=354 (M+1)

EXAMPLE 67

[7-Cyclopentylamino-5-(1,1-dioxo-thiomorpholin-4-yl-methyl)-1H-indol-2-yl]-pyrrolidin-1-yl-methanone

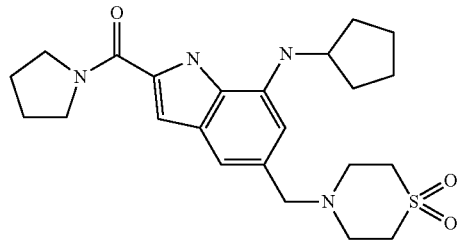

[7-Cyclopentylamino-5-(1,1-dioxo-11 ambda*6*-thiomorpholin-4-ylmethyl)-1H-indol-2-yl]-pyrrolidin-1-yl-methanone 5-(1,1-Dioxo-thiomorpholin-4-ylmethyl)-7-nitro-1H-indol-2-carboxylic acid obtained in Preparation Example 8, pyrrolidine and cyclopentanone were reacted in the same manner as in Example 1 to give the title compound.

MS[M+1]=445 (M+1)

EXPERIMENTAL EXAMPLE 1

Measurements and Analysis of the Example Compounds for the Hepatocyte Protective Effect Against the Substances Causing Hepatocyte Toxicity Various endogenous/exogenous attacks on cells trigger the mechanisms of cell death which is broadly classified into two types—i.e., apoptosis or necrosis. Using these cell death mechanisms, in the present experimental example, primary hepatocytes isolated from rats were treated with drugs which were clinically shown to result in serious side-effects of hepatocyte toxicity or various chemicals which cause cell death, and the compounds synthesized in the Examples were estimated for their hepatocyte protective effects, after 24-48 hours. The substances used to cause hepatocyte death include $CCl_4$, ActD, $H_2O_2$, doxorubicin, anti-Fas Ab/Actinomycin D, acetaminophen, EtOH, $CdCl_2$, palmitate, stearate, cyclophosphamide, terfenadine, diclofenac, simvastatin, and adefovir. Primary hepatocytes were isolated using the method of Seglen P O (Experimental Cell Research 74 (1972), pp. 450-454). Briefly, hepatocytes were isolated according to the two-step collagenase perfusion method, and dead cells were removed by low speed (500 rpm) centrifugation for 10 min using percoll gradient (Kreamer B L et al., In Vitro Cellular & Developmental Biology 22 (1986), pp. 201-211). During this step, the viability of cells was maintained 90% or above. The cells were suspended in HepatoZYME media (Gibco BRL), and the number of cells was counted. $1.5 \times 10^4$ cells in 100 µl were placed into the collagen-coated 96-well plate (BD Biocoat), and adhered on the bottom for 3-4 hours.

In order to assess the hepatocyte protective effect, the above adhered cells were pretreated with the Example compounds for 30 min. At this time, the concentration of the Example compounds was serially diluted by 2-fold or 3-fold over 5 steps starting from 30 µM, 10 µM or 1 µM depending on the experiments, and the final concentration of DMSO was adjusted to 0.2%. 30 min after the treatment by the compounds, the cells were treated by the substances deriving hepatocyte death or hepatotoxic drugs at the concentrations indicated in Table 1. After 24-48 hours, the viability of cells was determined to estimate the hepatocyte protective effects. The viability of cells was determined using the WST-1 (MK-400, Takeda) method by the absorbance at 440 nm. Hepatocyte protective effects of the Example compounds were represented by "$EC_{50}$" which was calculated from measured values. "$EC_{50}$" herein means the concentration of the compound at which 50% of maximum protective effect is observed in the experiment. Table 1 shows $EC_{50}$ of the representative Example compounds against doxorubicin treatment.

TABLE 1

| Example | $EC_{50}$ (µM) | Example | $EC_{50}$ (µM) | Example | $EC_{50}$ (µM) |
|---|---|---|---|---|---|
| 13 | 0.15 | 29 | 0.2 | 38 | 0.33 |
| 46 | 0.29 | 49 | 0.33 | 50 | 0.175 |
| 51 | 0.33 | 52 | 0.21 | 53 | 0.71 |
| 55 | 0.43 | 60 | 0.25 | | |

EXPERIMENTAL EXAMPLE 2

Protective Effects when tBHP (Tert-Butyl Hydroxy Peroxide; t-BuOOH) was Treated on Hepatocytes and Other Cells Derived from Various Tissues 1) Protective Effect when tBHP was Treated on Primary Hepatocytes Hepatocytes were isolated according to the same procedure as Experimental Example 1, suspended in DMEM (Gibco+10% FBS+1× antibiotics) media, and distributed to the plate. After 24 h from the distribution of hepatocytes, the compounds were serially diluted by 3-fold to the final concentration of 30, 10, 3, 1, 0.3, 0.1 µM, by which the cells were pretreated for 30 min. Cells were treated with tBHP at the final concentration of 300 µM, and the protective effects were determined after 1 hour. As in Experimental Example 1, after the treatment with WST-1 (Takeda, 10 µl) for 1.5 hours, $EC_{50}$ values were calculated by absorbance measurements at 440 nm using SpectraMax (Molecular Device).

2) Protective Effect when tBHP was Treated on Pancreatic Cells (Linm5F)

In order to determine the protective effect on pancreatic cells, Linm5F cells, a sort of the beta cells, were plated into a 96-well plate in the amount of $2 \times 10^4$ cells/well, and incubated for 24 hours. The Example compounds were serially diluted by 3-fold to the final concentration of 30, 10, 3, 1, 0.3 and 0.1 µM, by which each well was treated for 1 hour. Cells were treated with tBHP at the final concentration of 400 µM, and further incubated for 5 hours. Protective effects were determined using the SRB (Sulforhodamine B Protein) method in which the total amount of cellular protein is stained. Briefly, cells were incubated for 5 hours, 50 µl of 4% formaldehyde solution was added to each well to fix the cells, and stored for about 30 min at room temperature. After discarding the media, each well was washed with distilled water 2-3 times, and the plate was dried in an oven at 50° C. 50 µl of SRB solution was added to each well, and the plate was placed for about 30 min at room temperature. After removing SRB solution, the plate was washed with 1% acetic acid solution 2-3 times. After drying the plate in an oven at 50° C., 100 µl of 10 mM Tris solution was added to elute SRB which was staining the intracellular protein. Absorbance was measured at 590 nm and 650 nm using SpectraMax, and the absorbance at 650 nm was subtracted from the absorbance at 590 nm to calculate the $EC_{50}$ value.

3) Protective Effect when tBHP was Treated on Cardiac Cells (H9C2, White Rat Cardiomyocyte)

In order to assess the protective effect on cardiac cells, H9C2 cells were plated in the amount of $1.5 \times 10^4$ cells/well, and incubated for 24 hours. The Example compounds were serially diluted by 3-fold to the final concentrations of 30, 10, 3, 1, 0.3 and 0.1 µM, by which each well was treated for 45 min. Cells were treated with tBHP at the final concentration of 400 µM, and incubated for 2 hours. The protective effect of each compound was determined using the same SRB method as in Linm5F of above mentioned 2).

4) Protective Effect when tBHP was Treated on Kidney Cells (LLC-PK1)

In order to determine the protective effect on kidney cells, $4 \times 10^4$ cells were plated into each well, and incubated for 24 hours. Cells were treated with the Example compounds at the final concentration of 30, 10, 3, 1, 0.3 and 0.1 µM, and incubated for 30 min. Cells were treated with 400 µM tBHP, and further incubated for 6 hours. The protective effect of each compound was determined using the same SRB method as in Linm5F of the above-mentioned 2).

5) Protective Effect when tBHP was Treated on Chondrocytes

In order to determine the protective effect on chondrocytes, chondrocytes were isolated from the 2 hind legs of 16 week-old SD rats (body weight: 450-460 g). The isolation method was as follows. Cartilage isolated from the knee regions of rat hind legs was transferred to a 100 pi plate containing PBS (+1× antibiotics). PBS was maintained at 4° C. in an ice bath. PBS was exchanged with a fresh one and centrifuged at 1,000 rpm. After removal of PBS, 3 ml of 1× trypsin (Gibco) at the temperature of 37° C. was added and followed by treatment for 15 min. Supernatant was discarded after centrifugation and washed again with PBS. Supernatant was discarded after centrifugation. After the addition of 0.2% collagenase (Worthington, type II) thereto, the cells were isolated by the overnight incubation in a rotating 37° C. incubator. The filtered cell solution was centrifuged, and the supernatant was discarded. Following the washing with PBS, cells were suspended in 10 ml of DMEM/F-12 (Gibco, 10% FBS). $2 \times 10^4$ cells were distributed to each well and incubated for 24 hours. The Example compounds were serially diluted by 3-fold to the final concentrations of 30, 10, 3, 1, 0.3 and 0.1 µM, by which each well was treated for 1 hour. Cells were treated with tBHP at the final concentration of 500 µM and incubated for 3 hours. The protective effect of each compound was determined using the same SRB staining method as in Linm5F of the above-mentioned 2).

6) Protective Effect when tBHP was Treated on Neural Cells (SK-N-MC)

In order to assess the protective effect on brain cells, $2 \times 10^4$ brain cells were plated into a 96-well plate using DMEM media (Gibco, 10% FBS), and incubated for 24 hours. The Example compounds were serially diluted by 3-fold to the final concentrations of 30, 10, 3, 1, 0.3 and 0.1 µM, by which each well was treated for 1 hour. Cells were treated with tBHP at the final concentration of 400 µM and incubated for 6 hours. 50 µl of media was taken from each well to proceed with LDH assay (Promega). In the LDH assay, 50 µl of media was mixed with 50 µl of assay solution. After reaction for 30 min at room temperature, absorbance was measured at 490 nm using SpectraMax (Molecular Device).

INDUSTRIAL APPLICABILITY

As is demonstrated in above results, the novel compound according to the present invention not only exhibits the effects for hepatoprotection and hepatic functional improvement, but also can be useful for the prevention and treatment of chronic hepatic diseases such as fatty liver, hepatic fibrosis, hepatocirrhosis, etc. and acute/chronic hepatic diseases such as hepatitis, etc. caused by virus or drugs. The compound of the present invention also exhibits the necrosis inhibitory efficacy in cells from the pancreas, kidney, brain, cartilage, and heart.

Therefore, the compound of the present invention can be useful in the prevention and treatment of necrosis and associated diseases.

It would be within the ability of those skilled in the art to conduct various applications and modifications without departing from the scope of the present invention.

The invention claimed is:
1. An indole amide compound of the following Formula (1) or a pharmaceutically acceptable salt or isomer thereof:

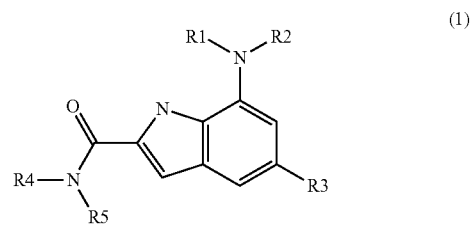

in which
R1 represents hydrogen, $C_1$—$C_6$-alkyl or —$CH_2)_n$—$C_3$-$C_8$-cycloalkyl;
n denotes a number of 0 to 2;
R2 represents —X—$CH_2)_n$-A-R6, wherein X represents a direct bond, A represents a direct bond, or represents $C_3$-$C_8$-cycloalkyl or $C_6$-$C_{10}$ aryl, or represents 4- to 8-membered heterocyclyl or heteroaryl each of which has 1 to 3 heteroatoms selected from N, O and S, R6 represents hydrogen, $C_1$-$C_6$-alkyl, halogen, hydroxy, amino, nitrile, nitro or —$CO_2$—R7, and R7 represents hydrogen, $C_1$-$C_6$-alkyl, $C_6$-$C_{10}$ aryl or $C_6$-$C_{10}$ aryl-$C_1$-$C_6$-alkyl, or represents 5- or 6-membered heterocyclyl or heteroaryl each of which optionally contains oxo, and has 1 to 3 heteroatoms selected from N, O and S, provided that R2 is not hydrogen;
R1 and R2 may together represent —(CH2)$_r$—, wherein r denotes a number of 4 to 6;
R3 represents halogen, hydroxy, —NH—R7 or —(CH$_2$)$_m$—R7, wherein m denotes a number of 0 to 3, provided that when m is 0, R7 is not hydrogen;
R4 represents —(CHR7)$_n$—B—(Z—R8)(Z'—R9), wherein B represents a direct bond, or represents $C_6$-$C_{10}$ aryl, or represents 4- to 9-membered heterocyclyl or heteroaryl each of which has 1 to 3 heteroatoms selected from N, O and S, Z and Z' independently of one another represent a direct bond, —(CH$_2$)$_m$—, —O— or —N—, and R8 and R9 independently of one another represent hydrogen, halogen, hydroxy, amino, di($C_1$-$C_6$-alkyl)amino, $C_1$-$C_6$-alkyl, —$CO_2$R7, $C_3$-$C_8$-cycloalkyl, $C_6$-$C_{10}$-aryl, $C_6$-$C_{10}$-aryloxy, $C_6$-$C_{10}$-aryl-$C_1$-$C_6$-alkyl or $C_6$-$C_{10}$-aryl-$C_1$-$C_6$-alkylamino, or represents 4- to 8-membered heterocyclyl which has 1 to 3 heteroatoms selected from N, O and S, provided that when B is direct bond, (Z'—R9) does not exist;
R5 represents —(CH$_2$)$_m$—R10, wherein R10 represents hydrogen, $C_1$-$C_6$-alkyl or $C_6$-$C_{10}$-aryl;
Z' and R5 may be connected with an atom(s) to which they are attached to form the structure

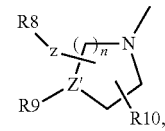

provided that when Z' is —O—, R9 does not exist;
where alkyl, alkoxy, aryl, cycloalkyl, heterocycle and heteroaryl may be optionally substituted, and the substituents are one or more selected from the group consisting of hydroxy, halogen, nitrile, amino, alkylamino, dialkylamino, carboxy, alkyl, alkoxy, arylalkoxy and oxo.

2. The compound according to claim 1, wherein
R1 represents hydrogen, $C_1$-$C_6$-alkyl or —$(CH_2)_n$—$C_3$-$C_8$-cycloalkyl;
n denotes a number of 0 to 2;
R2 represents —X—$(CH_2)_n$-A-R6, wherein X represents a direct bond, A represents a direct bond, or represents $C_4$-$C_8$-cycloalkyl or $C_6$-$C_{10}$ aryl, or represents 4- to 8-membered heterocyclyl or heteroaryl each of which has 1 to 3 heteroatoms selected from N, O and S, R6 represents hydrogen, $C_1$-$C_6$-alkyl, halogen, amino, nitrile or —$CO_2$—R7, and R7 represents hydrogen, $C_1$-$C_6$-alkyl, $C_6$-$C_{10}$ aryl or $C_6$-$C_{10}$ aryl-$C_1$-$C_6$-alkyl, or represents 5- or 6-membered heterocyclyl or heteroaryl each of which optionally contains oxo, and has 1 to 3 heteroatoms selected from N, O and S, provided that R2 is not hydrogen;
R1 and R2 may together represent —$(CH_2)_r$—, wherein r denotes a number of 4 to 6;
R3 represents halogen or $C_1$-$C_6$-alkyl;
R4 represents —$(CHR7)_n$—B—(Z—R8)(Z'—R9), wherein B represents a direct bond, or represents phenyl, or represents 4- to 9-membered heterocyclyl or heteroaryl each of which has 1 to 3 heteroatoms selected from N, 0 and S, Z and Z' independently of one another represent a direct bond, —$(CH_2)_m$—, —O— or —N—, m denotes a number of 0 to 3, and R8 and R9 independently of one another represent hydrogen, halogen, hydroxy, amino, di($C_1$-$C_6$-alkyl)amino, $C_1$-$C_6$-alkyl optionally substituted with halogen, —$CO_2$R7, $C_4$-$C_6$-cycloalkyl, $C_6$-$C_{10}$-aryl optionally substituted with halogen or $C_1$-$C_6$-alkyl, $C_6$-$C_{10}$-aryloxy optionally substituted with halogen, $C_6$-$C_{10}$-aryl-$C_1$-$C_6$-alkyl or $C_6$-$C_{10}$-aryl-$C_1$-$C_6$-alkylamino optionally substituted with halogen or di($C_1$-$C_6$-alkyl)amino, or represents 4- to 8-membered heterocyclyl which has 1 to 3 heteroatoms selected from N, O and S, provided that when B is direct bond, (Z'—R9) does not exist;
R5 represents —$(CH_2)_m$—R10, wherein R10 represents hydrogen, $C_1$-$C_6$-alkyl optionally substituted with amino or $C_6$-$C_{10}$-aryl optionally substituted with halogen;
Z' and R5 may be connected with an atom(s) to which they are attached to form the structure

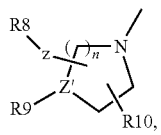

provided that when Z' is —O—, R9 does not exist.
3. The compound according to claim 1, which is the following Formula (1a) or (1b):

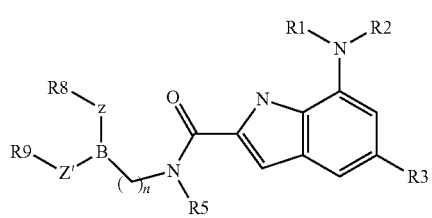

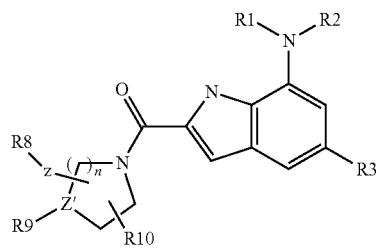

wherein R1, R2, R3, R5, R8, R9, R10, Z, Z', B and n are the same as defined in claim 1.
4. The compound according to claim 1, wherein R1 is hydrogen, isopentyl or cyclopentylmethyl.
5. The compound according to claim 1, wherein R2 represents —X—$(CH_2)_n$-A-R6, wherein n denotes a number of 0 to 2, X represents a direct bond, A represents a direct bond, or represents $C_3$-$C_6$-cycloalkyl or phenyl, or represents 4- to 6-membered heterocyclyl or heteroaryl each of which has 1 to 3 heteroatoms selected from N, O and S, and R6 represents hydrogen, $C_1$-$C_6$-alkyl, amino or —$CO_2H$, provided that R2 is not hydrogen.
6. The compound according to claim 5, wherein R2 is cyclopentyl, piperidine, isopentyl, cyclopentylmethyl, phenethyl, pentyl, cyclopropylmethyl, 2-aminopyridin-3-ylmethyl, thiazolmethyl, pyrrolidine, pyrrolidin-2-ylmethyl, piperidin-3-yl, aminomethylcarbonyl, acetic acid, tetrahydropyran or cyclohexyl.
7. The compound according to claim 1, wherein R1 and R2 together represent —$(CH_2)_5$—.
8. The compound according to claim 1, wherein R3 is halogen or $C_1$-$C_3$-alkyl.
9. The compound according to claim 8, wherein R3 is chloro, bromo or methyl.
10. The compound according to claim 1, wherein B of R4 represents a direct bond, or represents phenyl, pyrrolidine, morpholine, thiazole or indazole.
11. The compound according to claim 1, wherein Z and Z' of R4 independently of one another represent —$(CH_2)_m$—, —O— or —N—.
12. The compound according to claim 1, wherein R8 of R4 represents hydrogen, halogen, hydroxy, amino, di($C_1$-$C_6$-alkyl)amino, $C_1$-$C_6$-alkyl optionally substituted with halogen, —$CO_2R7$ (R7 represents hydrogen or $C_1$-$C_3$-alkyl), $C_4$-$C_6$-cycloalkyl, phenyl optionally substituted with halogen or $C_1$-$C_3$-alkyl, phenoxy optionally substituted with halogen, phenyl-$C_1$-$C_3$-alkyl or benzylamino optionally substituted with halogen or di($C_1$-$C_3$-alkyl)amino, or represents 5- or 6-membered heterocyclyl which has 1 or 2 heteroatoms selected from N, O and S.
13. The compound according to claim 12, wherein R8 is dimethylamino, amino, isopentyl, fluoro, 3,5-dimethyl-phenyl, difluoromethyl, phenyl, benzyl, isopropyl, cyclopentyl, phenoxy, 3,4-difluorophenoxy, 3-dimethylamino-benzylamino, 3,5-difluorobenzylamino, hydroxy, carboxy, piperidine, methoxycarbonyl or pyrrolidine.
14. The compound according to claim 1, wherein R9 of R4 is hydrogen, phenoxy or benzyl.
15. The compound according to claim 1, wherein R10 of R5 is hydrogen, 2,4-difluorophenyl, 4-fluorophenyl or aminomethyl.
16. An indole amide compound which is selected from the following group:

5-Chloro-7-cyclopentylamino-1H-indol-2-carboxylic acid (4-phenoxy-phenyl)-amide;
5-Chloro-7-(pyrrolidin-3-ylamino)-1H-indol-2-carboxylic acid (4-phenoxy-phenyl)-amide;
5-Chloro-7-(piperidin-4-ylamino)-1H-indol-2-carboxylic acid [4-(3,4-difluoro-phenoxy)-phenyl]-amide;
5-Chloro-7-(piperidin-4-ylamino)-1H-indol-2-carboxylic acid (3-phenoxy-phenyl)-amide;
5-Chloro-7-[(pyrrolidin-2-ylmethyl)-amino]-1H-indol-2-carboxylic acid benzylamide;
5-Chloro-7-(piperidin-3-ylamino)-1H-indol-2-carboxylic acid (4-phenoxy-phenyl)-amide;
5-Chloro-7-(piperidin-4-ylamino)-1H-indol-2-carboxylic acid (4-phenoxy-phenyl)-amide;
5-Chloro-7-[(pyrrolidin-2-ylmethyl)-amino]-1H-indol-2-carboxylic acid (3-phenoxy-phenyl)-amide;
5-Chloro-7-[(pyrrolidin-2-ylmethyl)-amino]-1H-indol-2-carboxylic acid (3-cyclopentyloxy-5-phenoxy-phenyl)-amide;
5-Chloro-7-[(pyrrolidin-2-ylmethyl)-amino]-1H-indol-2-carboxylic acid (4-phenoxy-phenyl)-amide;
7-[(2-Amino-pyridin-3-ylmethyl)-amino]-5-chloro-1H-indol-2-carboxylic acid [4-(3,4-difluoro-phenoxy)-phenyl]-amide;
5-Chloro-7-(piperidin-4-ylamino)-1H-indol-2-carboxylic acid (3-cyclopentyloxy-phenyl)-amide;
5-Chloro-7-(piperidin-4-ylamino)-1H-indol-2-carboxylic acid (3-morpholin-4-ylmethyl-phenyl)-amide;
5-Chloro-7-(piperidin-4-ylamino)-1H-indol-2-carboxylic acid biphenyl-3-ylamide;
5-Chloro-7-(piperidin-4-ylamino)-1H-indol-2-carboxylic acid (3-benzyloxy-phenyl)-amide;
5-Chloro-7-(piperidin-4-ylamino)-1H-indol-2-carboxylic acid (4-trifluoromethoxy-phenyl)-amide;
5-Chloro-7-(piperidin-4-ylamino)-1H-indol-2-carboxylic acid [4-(3,5-dimethyl-phenoxy)-phenyl]-amide;
5-Chloro-7-(piperidin-4-ylamino)-1H-indol-2-carboxylic acid [2-(3-fluoro-phenyl)-ethyl]-amide;
5-Chloro-7-[(thiazol-2-ylmethyl)-amino]-1H-indol-2-carboxylic acid (3-phenoxy-phenyl)-amide;
5-Chloro-7-(piperidin-4-ylamino)-1H-indol-2-carboxylic acid (4-isopentyloxy-phenyl)-amide;
5-Chloro-7-[(pyrrolidin-2-ylmethyl)-amino]-1H-indol-2-carboxylic acid [4-(3,4-dimethyl-phenoxy)-phenyl]-amide;
(5-Chloro-7-cyclopentylamino-1H-indol-2-yl)-pyrrolidin-1-yl-methanone;
(R)-1-(5-chloro-7-cyclopentylamino-1H-indol-2-carbonyl)-pyrrolidin-3-carboxylic acid methyl ester;
(S)-1-(5-chloro-7-cyclopentylmethylamino-1H-indol-2-carbonyl)-pyrrolidin-3-carboxylic acid methyl ester;
(R)-1-[5-chloro-7-(tetrahydro-pyran-4-ylamino)-1H-indol-2-carbonyl]-pyrrolidin-3-carboxylic acid methyl ester;
(S)-1-[5-methyl-7-(tetrahydro-pyran-4-ylamino)-1H-indol-2-carbonyl]-pyrrolidin-3-carboxylic acid methyl ester;
(5-Bromo-7-cyclohexylamino-1H-indol-2-yl)-morpholin-4-yl-methanone;
(7-Cyclopentylamino-5-methyl-1H-indol-2-yl)-morpholin-4-yl-methanone;
(7-Cyclopentylamino-5-methyl-1H-indol-2-yl)-piperazin-4-yl-methanone;
5-Chloro-7-cyclopentylamino-1H-indol-2-carboxylic acid (1-benzyl-pyrrolidin-3-ylmethyl)-amide;
7-Cyclopentylamino-5-methyl-1H-indol-2-carboxylic acid (2-dimethylamino-ethyl)-amide;
7-Cyclopentylamino-5-methyl-1H-indol-2-carboxylic acid (2-morpholin-4-yl-ethyl)-amide;
(4-Benzyl-piperazin-1-yl)-[5-chloro-7-(piperidin-4-ylamino)-1H-indol-2-yl]-methanone;
[5-Chloro-7-(piperidin-4-ylamino)-1 H-indol-2-yl]-[(R)-3-(3,4-difluoro-phenoxymethyl)-pyrrolidin-1-yl]-methanone;
[5-Chloro-7-(piperidin-4-ylamino)-1H-indol-2-yl]-((R)-3-phenoxymethyl-pyrrolidin-1-yl)-methanone;
(R)-1-[5-chloro-7-(tetrahydro-pyran-4-ylamino)-1H-indol-2-carbonyl]-pyrrolidin-3-carboxylic acid;
[5-Chloro-7-(tetrahydropyran-4-ylamino)-1H-indol-2-yl]-((R)-3-hydroxymethyl-pyrrolidin-1-yl)-methanone;
(S)-1-[5-methyl-7-(tetrahydropyran-4-ylamino)-1H-indol-2-carbonyl]-pyrrolidin-3-carboxylic acid;
7-(2-Amino-acetylamino)-5-chloro-1H-indol-2-carboxylic acid (4-phenoxy-phenyl)-amide;
(3-Aminomethyl-pyrrolidin-1-yl)-(5-chloro-7-cyclopentylamino-1H-indol-2-yl)-methanone;
(5-Chloro-7-cyclopentylamino-1H-indol-2-yl)-(3-piperidin-1-ylmethyl-pyrrolidin-1-yl)-methanone;
[5-Chloro-7-(tetrahydro-pyran-4-ylamino)-1H-indol-2-yl]-(3-piperidin-1-ylmethyl-pyrrolidin-1-yl)-methanone;
(3-Aminomethyl-pyrrolidin-1-yl)-[5-chloro-7-(tetrahydro-pyran-4-ylamino)-1H-indol-2-yl]-methanone;
((R)-3-amino-pyrrolidin-1-yl)-[5-chloro-7-cyclopentylamino-1H-indol-2-yl]-methanone;
(5-Chloro-7-cyclopentylamino-1H-indol-2-yl)-{3-[(3-dimethylamino-benzylamino)-methyl]-pyrrolidin-1-yl}-methanone;
(3-Aminomethyl-pyrrolidin-1-yl)-[5-chloro-7-(3-methyl-butylamino)-1H-indol-2-yl]-methanone;
(3-Aminomethyl-pyrrolidin-1-yl)-[5-chloro-7-(cyclopentylmethyl-amino)-1H-indol-2-yl]-methanone;
(3-Aminomethyl-pyrrolidin-1-yl)-(5-chloro-7-piperidin-1-yl-1H-indol-2-yl]-methanone;
(3-Aminomethyl-pyrrolidin-1-yl)-(5-chloro-7-penethyl-amino-1H-indol-2-yl]-methanone;
(3-Aminomethyl-pyrrolidin-1-yl)-(5-chloro-7-pentylamino-1H-indol-2-yl]-methanone;
(3-Aminomethyl-pyrrolidin-1-yl-(5-chloro-7-cyclohexylamino-1H-indol-2-yl]-methanone;
(3-Aminomethyl-piperidin-1-yl)-(5-chloro-7-cyclopentylamino-1H-indol-2-yl]-methanone;
(3-Aminomethyl-pyrrolidin-1-yl)-[7-(bis-cyclopropylmethyl-amino)-5-chloro-1H-indol-2-yl]-methanone;
(3-Aminomethyl-pyrrolidin-1-yl)-{7-[bis-(3-methyl-butyl)-amino]-5-chloro-1H-indol-2-yl}-methanone;
((S)-3-amino-pyrrolidin-1-yl)-(5-chloro-7-cyclopentylamino-1H-indol-2-yl}-methanone;
{7-[Bis-(3-methyl-butyl)-amino]-5-chloro-1H-indol-2-yl}-[3-(4-fluoro-benzylaminomethyl)-pyrrolidin-1-yl]-methanone;
{7-[Bis-(3-methyl-butyl)-amino]-5-chloro-1H-indol-2-yl}-[3-(3 ,4-difluoro-benzylaminomethyl)-pyrrolidin-1-yl]-methanone;
(3-Aminomethyl-pyrrolidin-1-yl)-(5-bromo-7-cyclopentylamino-1H-indol-2-yl)-methanone;
7-Cyclopentylamino-5-methyl-1H-indol-2-carboxylic acid (pyrrolidin-3-ylmethyl)-amide;
{7-[Bis-(3-methyl-butyl)-amino]-5-chloro-1H-indol-2-yl}-[(3R,4R)-3-(2,4-difluoro-phenyl)-4-pyrrolidin-1-ylmethyl-pyrrolidin-1-yl]-methanone;
{7-[Bis-(3-methyl-butyl)-amino]-5-chloro-1H-indol-2-yl}-[(3R,4R)-3-(4-chloro-phenyl)-4-pyrrolidin-1-ylmethyl-pyrrolidin-1-yl]-methanone;

(5-Chloro-7-cyclopentylamino-1H-indol-2-yl}-[(3R,4R)-3-(2,4-difluoro-phenyl)-4-pyrrolidin-1-ylmethyl-pyrrolidin-1-yl]-methanone;

(5-Chloro-7-(tetrahydropyran-4-ylamino)-1H-indol-2-yl}-[(3R,4R)-3-(2,4-difluoro-phenyl)-4-pyrrolidin-1-ylmethyl-pyrrolidin-1-yl]-methanone;

(5-Chloro-7-(piperidin-4-ylamino)-1H-indol-2-yl}-[(3R,4R)-3-(2,4-difluoro-phenyl)-4-pyrrolidin-1-ylmethyl-pyrrolidin-1-yl]-methanone;

(5-Chloro-7-cyclopentylamino)-1H-indol-2-carboxylic acid ((R)-2-phenyl-1-pyrrolidin-1-ylmethyl-ethyl)-amide;

[5-Methyl-2-(pyrrolidin-1-carbonyl)-1H-indol-7-ylamino]-acetic acid; and

[7-Cyclopentylamino-5-(1,1-dioxo-thiomorpholin-4-yl-methyl)-1H-indol-2-yl]-pyrrolidin-1-yl-methanone, or a pharmaceutically acceptable salt or isomer thereof.

17. A composition, which comprises a therapeutically effective amount of the compounds of Formula (1), a pharmaceutically acceptable salt or isomer thereof as defined in claim 1 as an active ingredient together with a pharmaceutically acceptable carrier or diluent.

18. A method of preparing a composition, which comprises the step of mixing the compound of Formula (1), a pharmaceutically acceptable salt or isomer thereof as defined in claim 1 as an active ingredient together with a pharmaceutically acceptable carrier.

\* \* \* \* \*